(12) United States Patent
Davis et al.

(10) Patent No.: US 12,194,042 B2
(45) Date of Patent: Jan. 14, 2025

(54) USES

(71) Applicant: INTRA-CELLULAR THERAPIES, INC., New York, NY (US)

(72) Inventors: Robert E. Davis, San Diego, CA (US); Kimberly E. Vanover, New York, NY (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 762 days.

(21) Appl. No.: 17/287,478

(22) PCT Filed: Oct. 21, 2019

(86) PCT No.: PCT/US2019/057260
§ 371 (c)(1),
(2) Date: Apr. 21, 2021

(87) PCT Pub. No.: WO2020/086481
PCT Pub. Date: Apr. 30, 2020

(65) Prior Publication Data
US 2021/0379072 A1    Dec. 9, 2021

Related U.S. Application Data

(60) Provisional application No. 62/748,517, filed on Oct. 21, 2018.

(51) Int. Cl.
*A61K 31/519* (2006.01)
*A61P 25/16* (2006.01)
*C07D 487/14* (2006.01)

(52) U.S. Cl.
CPC ............ *A61K 31/519* (2013.01); *A61P 25/16* (2018.01)

(58) Field of Classification Search
CPC ...... A61K 31/519; A61P 25/16; C07D 487/14
See application file for complete search history.

(56) References Cited

U.S. PATENT DOCUMENTS

| 6,943,171 B2 | 9/2005 | Asberom et al. |
| 7,964,607 B2 | 6/2011 | Verhoest et al. |

(Continued)

FOREIGN PATENT DOCUMENTS

| WO | WO-2009/075784 A1 | 6/2009 |
| WO | WO 2010/098839 A1 | 9/2010 |
| WO | WO-2018/069312 A1 | 4/2018 |

OTHER PUBLICATIONS

Goetz et al. Movement Disorder Society UPDRS Revision Task Force. Movement Disorder Society-sponsored revision of the Unified Parkinson's Disease Rating Scale (MDS-UPDRS): scale presentation and clinimetric testing results. Mov Disord. Nov. 15, 2008;23(15):2129-70. (Year: 2008).*

(Continued)

*Primary Examiner* — Bruck Kifle
*Assistant Examiner* — Kevin S Martin
(74) *Attorney, Agent, or Firm* — Hoxie & Associates LLC

(57) ABSTRACT

The disclosure provides methods, treatments and materials for treating diseases or disorders associated with the dopamine D1 receptor intracellular pathway. In particular, the present disclosure provides for methods of treating such diseases and disorders in combination with a dopamine replacement therapy.

18 Claims, 2 Drawing Sheets

(56) References Cited

U.S. PATENT DOCUMENTS

| | | | |
|---|---|---|---|
| 8,273,751 B2* | 9/2012 | Li | A61P 5/24 544/246 |
| 9,403,836 B2* | 8/2016 | Li | A61P 25/18 |
| 2013/0085123 A1 | 4/2013 | Li et al. | |
| 2017/0291904 A1 | 10/2017 | Li et al. | |

OTHER PUBLICATIONS

Goetz CG, Nutt JG, Stebbins GT. The Unified Dyskinesia Rating Scale: presentation and clinimetric profile. Mov Disord. Dec. 15, 2008;23(16):2398-403. doi: 10.1002/mds.22341. PMID: 19025759. (Year: 2008).*

Hauser RA, Deckers F, Lehert P. Parkinson's disease home diary: further validation and implications for clinical trials. Mov Disord. Dec. 2004;19(12):1409-13. doi: 10.1002/mds.20248. PMID: 15390057. (Year: 2004).*

Cleveland Clinic, Dopamine Agonists, 2024, https://my.clevelandclinic.org/health/treatments/24958-dopamine-agonists. See attached PDF. (Year: 2024).*

Cardinale et al., "Inhibition of Phosphodiesterases as a Strategy to Achieve Neuroprotection in Huntington's Disease," CNS Neurosci Ther., vol. 24, p. 319-328, (2018).

Gupta et al., "Protective Effects of Phosphodiesterase-1 (PDE1) and ATP Sensitive Potassium (KATP) Channel Modulators Against 3-nitropropionic Acid Induced Behavioral and Biochemical Toxicities in Experimental Huntington's Disease," European Journal of Pharmacology, vol. 732, p. 111-122, (2014).

Li et al., "Discovery of Potent and Selective Inhibitors of Phosphodiesterase 1 for the Treatment of Cognitive Impairment Associated with Neurodegenerative and Neuropsychiatric Diseases," Journal of Medicinal Chemistry, vol. 59, p. 1149-1164, (2016).

Press Release, "Intra-Cellular Therapies Presents Results from ITI-214 Phase 1/2 Clinical Trial in Patients with Parkinson's Disease at 2018 American Neurological Association Annual Meeting," Intra-Cellular Therapies, 3 pages, Press Release Date: Oct. 17, 2018, (https://ir.intracellulartherapies.com/node/10026/pdf).

Press Release, "Intra-Cellular Therapies Presents Data on ITI-214 at the 2018 American Academy of Neurology Annual Meeting," Intra-Cellular Therapies, 5 pages, Press Release Date: Apr. 26, 2018, (https://ir.intracellulartherapies.com/news-releases/news-release-details/intra-cellular-therapies-presents-data-iti-214-2018-american), accessed on Nov. 14, 2019.

Davis et al., "M217. A Phase I/II Clinical Study of ITI-214, a Novel Phosphodiesterase I Inhibitor, for the Treatment of Motor and Non-Motor Symptoms of Parkinson's Disease," *Annals of Neurology*, vol. 84, Suppl. No. 22, 2 pages, (2018); Abstract Only.

Giorgi et al., "Lowered cAMP and cGMP Signalling in the Brain During Levodopa-induced Dyskinesias in Hemiparkinsonian Rats: New Aspects in the Pathogenetic Mechanisms," *European Journal of Neuroscience*, vol. 28, p. 941-950, (2008).

Höllerhage et al., "Protective Efficacy of Phosphodiesterase-1 Inhibition Against Alpha-synuclein Toxicity Revealed by Compound Screening in LUHMES Cells," *Scientific Reports*, vol. 7, No. 11469, 15 pages, (2017).

Medina et al., "Therapeutic Utility of Phosphodiesterase Type I Inhibitors in Neurological Conditions," *Frontiers in Neuroscience*, vol. 5, No. 21, 5 pages, (2011).

Niccolini et al., "Molecular Imaging of Levodopa-induced Dyskinesias," *Cellular and Molecular Life Sciences*, vol. 72, p. 2107-2117, (2015).

* cited by examiner

USES

CROSS-REFERENCE TO RELATED APPLICATIONS

This application is a U.S. National Stage application under 35 U.S.C. § 371 of International Application No. PCT/US2019/057260, filed on Oct. 21, 2019, which claims priority to and the benefit of U.S. Provisional Application Ser. No. 62/748,517, which was filed on Oct. 21, 2018, the contents of each of which are hereby incorporated by reference in their entireties.

FIELD OF THE DISCLOSURE

The field of the present disclosure relates to the treatment of diseases involving disorders of the dopamine D1 receptor intracellular pathway, such as Parkinson's disease, with PDE1 inhibitors in combination with dopamine replacement therapies (e.g., dopaminergic agonists). In particular embodiments, the present disclosure involves methods for treating motor impairment, enhancing the efficacy of a dopaminergic agonist and/or reducing the side effects of a dopaminergic agonist.

BACKGROUND

Eleven families of phosphodiesterases (PDEs) have been identified but only PDEs in Family I, the Ca2+-calmodulin-dependent phosphodiesterases (CaM-PDEs), have been shown to mediate the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyrus, olfactory tract and cerebellum, and its expression correlates with brain regions having high levels of dopamninergic innervation. Although PDE1B is primarily expressed in the central nervous system, it may be detected in the heart. PDE1C is primarily expressed in olfactory epithelium, cerebellar granule cells, and striatum. PDE1C is also expressed in the heart and vascular smooth muscle.

Cyclic nucleotide phosphodiesterases decrease intracellular cAMP and cGMP signaling by hydrolyzing these cyclic nucleotides to their respective inactive 5'-monophosphates (5'AMP and 5'GMP). CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of calcium dependent nucleotide cyclases, resulting in increased cAMP and cGMP. These cyclic nucleotides in turn activate protein kinase A (PKA; cAMP-dependent protein kinase) and/or protein kinase G (PKG; cAMP-dependent protein kinase) that phosphorylate downstream signal transduction pathway elements such as DARPP-32 (dopamine and cAMP-regulated phosphoprotein) and cAMP responsive element binding protein (CREB).

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP) or endorphin intracellular signaling pathway. For example, inhibition of PDE1B should act to potentiate the effect of a dopamine D1 agonist by protecting cGMP and cAMP from degradation, and should similarly inhibit dopamine D2 receptor signaling pathways, by inhibiting PDE1 activity. Chronic elevation in intracellular calcium is linked to cell death in numerous disorders, particularly in neurodegenerative diseases such as Alzheimer's, Parkinson's and Huntington's Diseases, and in disorders of the circulatory system leading to stroke and myocardial infarction. PDE1 inhibitors are therefore potentially useful in diseases characterized by reduced dopamine D1 receptor signaling activity, such as Parkinson's disease, restless leg syndrome, depression, and cognitive impairment.

Over 1.0 million and 1.2 million patients in the United States and Europe, respectively, live with Parkinson's disease. Parkinson's Disease is a progressive neurodegenerative disorder largely affecting dopamine systems in the brain and characterized by motor impairment and nonmotor symptoms, including but not limited to excessive daytime sleepiness, cognitive impairment, mood disorders and dysautonomia. Dopamine replacement therapies, such as with L-DOPA, address early motor symptoms, but are insufficient as the disease progresses and have limiting side effects. There remains a large unmet need for effective treatments to sustain the utility of dopaminergic therapies, and to address motor and nonmotor symptoms, while reducing the side effects of existing therapies.

SUMMARY

Provided herein are methods of treatment for treating a diseases or disorders associated with the dopamine D1 receptor intracellular pathway in patients currently being treated with known dopamine replacement therapies. Disorders such as Parkinson's Disease are in part characterized by an impaired ability to express habitual-automatic actions due to the loss of dopamine in the dorsolateral striatum, the region of the basal ganglia associated with the control of habitual behavior. Dopamine replacement therapy compensates for the lack of dopamine, representing the standard treatment for different motor symptoms of Parkinson's Disease, such as rigidity, bradykinesia and resting tremors. The dopamine precursor levodopa (L-DOPA), dopamine agonists (DAs), and enzyme inhibitors such as monoamine oxidase (MAO)-B inhibitors, catechol-O-methyltrasferase (COMT) inhibitors, and carbodopa, are commonly used in dopamine replacement therapies. However, dopamine replacement therapy causes several well-known complications, such as dyskinesias, motor fluctuations, and dopamine dysregulation syndrome.

The inventors have surprisingly found that administration of a PDE1 inhibitor to a patient suffering from such a disease or disorder enhances the positive effects of dopamine replacement therapy, while also mitigating the negative side effects commonly associated with such therapies. The PDE1 inhibitors disclosed herein induced these positive effects when administered with a variety of dopaminergic agonists. Thus, the present disclosure provides for compositions, methods and combination therapies capable of sustaining the utility of dopaminergic therapies while simultaneously addressing nonmotor symptoms.

Thus, in some embodiments, the present disclosure provides for a method of mitigating the side effects of a dopamine replacement therapy, the method comprising administering a pharmaceutically effective amount of a PDE1 inhibitor (i.e., a compound according to Formula I, II, III, or IV) to a subject in need thereof. In some aspects of the embodiments, the side effects encompass dyskinesias and motor impairment. In certain aspects of the embodiments, the dopaminergic agonist is administered as a dopamine replacement therapy to a subject in need thereof (i.e., a patient suffering from Parkinson's Disease receiving dopamine replacement therapy).

In other embodiments, the present disclosure provides for a method of enhancing the efficacy of a dopamine replacement therapy, the method comprising administering a pharmaceutically effective amount of a PDE1 inhibitor (i.e., a compound according to Formula I, II, III, or IV) to a patient in need thereof. In certain aspects of the embodiments, the dopamine replacement theraply is administered as a dopaminergic agonist to a subject in need thereof (i.e., a patient suffering from Parkinson's Disease).

In some embodiments, the present disclosure provides for a method of treating a diseases or disorders associated with the dopamine D1 receptor intracellular pathway (e.g., Parkinson's disease), the method comprising administering a pharmaceutically effective amount of a PDE1 inhibitor (i.e., a compound according to Formula I, II, III, or IV) in combination with a dopamine replacement therapy to a subject in need thereof.

In some embodiments, the present disclosure provides for a method of enhancing cGMP and/or cAMP signaling in a subject suffering from dyskinesias and/or motor impairment, the method comprising administering a pharmaceutically effective amount of a PDE1 inhibitor (i.e., a compound according to Formula I, II, III, or IV) to a subject in need thereof. In various aspects of the embodiments, the dyskinesias and/or motor impairment are consequent to dopamine replacement therapy (e.g., administration of a dopaminergic agonist).

In some embodiments, the present disclosure provides for a combination therapy comprising a PDE1 inhibitor (e.g., a compound according to Formula I, II, III, or IV) and a dopaminergic agonist (e.g., L-dopa and carbidopa).

BRIEF DESCRIPTION OF THE FIGURES

Other aspects, features, benefits and advantages of the embodiments will be apparent with regard to the following description, claims and figures.

DETAILED DESCRIPTION OF THE DISCLOSURE

Figure 1:
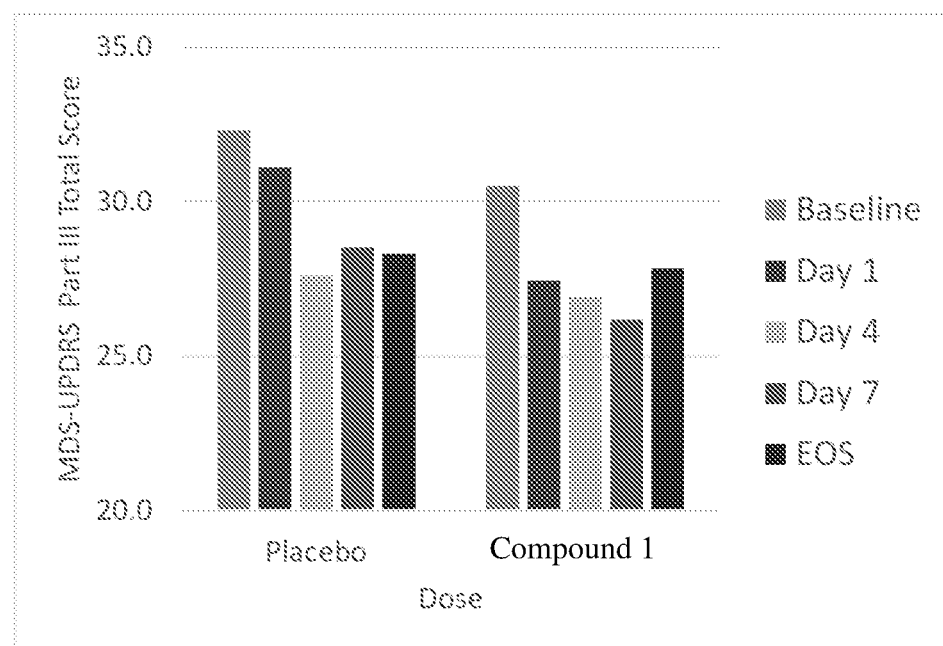
FIG. 1 shows the effect Compound 1 had on patients in UPDRS (Unified Parkinson's Disease Rating Scale) testing. Compound 1 was shown to decrease scores by day 7. Scores increase at end of study (EOS), 30 days after cessation of Compound 1 treatment.

In some embodiments, the PDE1 inhibitors for use in the methods of treatment and prophylaxis described herein are selective PDE1 inhibitors.

PDE1 Inhibitors

In one embodiment the invention provides that the PDE1 inhibitors for use in the methods of treatment and prophylaxis described herein are compounds of Formula I:

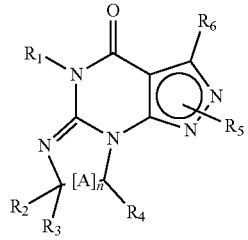

Formula I wherein
(i) $R_1$ is H or $C_{1-4}$ alkyl (e.g., methyl);
(ii) $R_4$ is H or $C_{1-4}$ alkyl and $R_2$ and $R_3$ are, independently, H or $C_{1-4}$ alkyl (e.g., $R_2$ and $R_3$ are both methyl, or $R_2$ is H and $R_3$ is isopropyl), aryl, heteroaryl, (optionally hetero)arylalkoxy, or (optionally hetero)arylalkyl; or $R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(iii) $R_5$ is a substituted heteroarylalkyl, e.g., substituted with haloalkyl; or $R_5$ is attached to one of the nitrogens on the pyrazolo portion of Formula I and is a moiety of Formula A

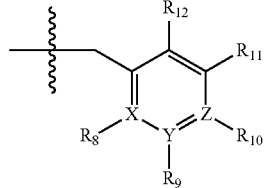

Formula A wherein X, Y and Z are, independently, N or C, and $R_8$, $R_9$, $R_{11}$ and $R_{12}$ are independently H or halogen (e.g., Cl or F), and $R_{10}$ is halogen, alkyl, cycloalkyl, haloalkyl (e.g., trifluoromethyl), aryl (e.g., phenyl), heteroaryl (e.g., pyridyl (for example pyrid-2-yl) optionally substituted with halogen, or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, $R_8$, $R_9$, or $R_{10}$, respectively, is not present; and (iv) $R_6$ is H, alkyl, aryl, heteroaryl, arylalkyl (e.g., benzyl), arylamino (e.g., phenylamino), heterarylamino, N,N-dialkylamino, N,N-diarylamino, or N-aryl-N-(arylakyl) amino (e.g., N-phenyl-N-(1,1'-biphen-4-ylmethyl) amino); and (v) n=0 or 1;

(vi) when n=1, A is —C($R_{13}R_{14}$)—
wherein $R_{13}$ and $R_{14}$, are, independently, H or $C_{1-4}$ alkyl, aryl, heteroaryl, (optionally hetero)arylalkoxy or (optionally hetero)arylalkyl;
in free, salt or prodrug form, including its enantiomers, diastereoisomers and racemates.

In another embodiment the invention provides that the PDE1 inhibitors for use in the methods of treatment and prophylaxis described herein are compounds of Formula II:

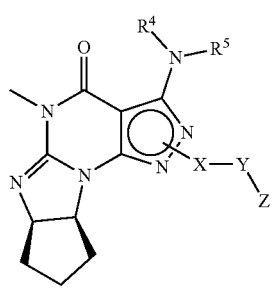

Formula II (i) X is $C_{1-6}$alkylene (e.g., methylene, ethylene or prop-2-yn-1-ylene);
(ii) Y is a single bond, alkynylene (e.g., —C≡C—), arylene (e.g., phenylene) or heteroarylene (e.g., pyridylene);
(iii) Z is H, aryl (e.g., phenyl), heteroaryl (e.g., pyridyl, e.g., pyrid-2-yl), halo (e.g., F, Br, Cl), halo$C_{1-6}$alkyl (e.g., trifluoromethyl), —C(O)—$R^1$, —N($R^2$)($R^3$), or $C_{3-7}$cycloalkyl optionally containing at least one atom selected from a group consisting of N or O (e.g., cyclopentyl, cyclohexyl, tetrahydro-2H-pyran-4-yl, or morpholinyl);
(iv) $R^1$ is $C_{1-6}$alkyl, halo$C_{1-6}$alkyl, —OH or —O$C_{1-6}$alkyl (e.g., —OCH$_3$);
(v) $R^2$ and $R^3$ are independently H or $C_{1-6}$alkyl;
(vi) $R^4$ and $R^5$ are independently H, $C_{1-6}$alky or aryl (e.g., phenyl) optionally substituted with one or more halo (e.g., fluorophenyl, e.g., 4-fluorophenyl), hydroxy (e.g., hydroxyphenyl, e.g., 4-hydroxyphenyl or 2-hydroxyphenyl) or $C_{1-6}$alkoxy;
(vii) wherein X, Y and Z are independently and optionally substituted with one or more halo (e.g., F, Cl or Br), $C_{1-6}$alkyl (e.g., methyl), halo$C_{1-6}$alkyl (e.g., trifluoromethyl), for example, Z is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-6}$alkyl (e.g., 5-trifluoromethylpyrid-2-yl) or $C_{1-6}$-alkyl (e.g., 5-methylpyrid-2-yl), or Z is aryl, e.g., phenyl, substituted with one or more halo (e.g., 4-fluorophenyl), in free, pharmaceutically acceptable salt or prodrug form, including its enantiomers, diastereoisomers and racemates.

In yet another embodiment the invention provides that the PDE1 inhibitors for use in the methods of treatment and prophylaxis described herein are Formula III:

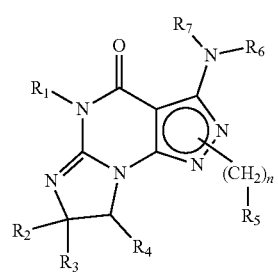

Formula III wherein
(i) $R_1$ is H or $C_{1-4}$ alkyl (e.g., methyl or ethyl);
(ii) $R_2$ and $R_3$ are independently H or $C_{1-6}$ alkyl (e.g., methyl or ethyl);
(iii) $R_4$ is H or $C_{1-4}$ alkyl (e.g., methyl or ethyl);
(iv) $R_5$ is aryl (e.g., phenyl) optionally substituted with one or more groups independently selected from —C(=O)—$C_{1-6}$ alkyl (e.g., —C(=O)—CH$_3$) and $C_{1-6}$-hydroxyalkyl (e.g., 1-hydroxyethyl);
(v) $R_6$ and $R_7$ are independently H or aryl (e.g., phenyl) optionally substituted with one or more groups independently selected from $C_{1-6}$ alkyl (e.g., methyl or ethyl) and halogen (e.g., F or Cl), for example unsubstituted phenyl or phenyl substituted with one or more halogen (e.g., F) or phenyl substituted with one or more $C_{1-6}$ alkyl and one or more halogen or phenyl substituted with one $C_{1-6}$ alkyl and one halogen, for example 4-fluorophenyl or 3,4-difluorophenyl or 4-fluoro-3-methylphenyl; and
(vi) n is 1, 2, 3, or 4, in free, pharmaceutically acceptable salt or prodrug form, including its enantiomers, diastereoisomers and racemates.

In yet another embodiment the invention provides that the PDE1 inhibitors for use in the methods of treatment and prophylaxis described herein are Formula IV:

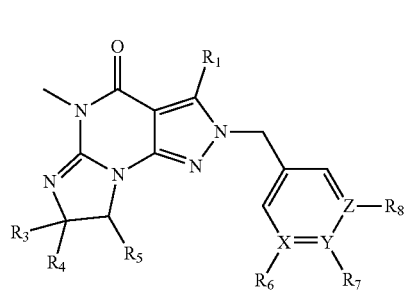

Formula IV in free or salt form, wherein
(i) $R_1$ is $C_{1-4}$alkyl (e.g., methyl or ethyl), or —NH($R_2$), wherein $R_2$ is phenyl optionally substituted with halo (e.g., fluoro), for example, 4-fluorophenyl;
(ii) X, Y and Z are, independently, N or C;

(iii) $R_3$, $R_4$ and $R_5$ are independently H or $C_{1-4}$alkyl (e.g., methyl); or $R_3$ is H and $R_4$ and $R_5$ together form a tri-methylene bridge (pref. wherein the $R_4$ and $R_5$ together have the cis configuration, e.g., where the carbons carrying $R_4$ and $R_5$ have the R and S configurations, respectively), (iv) $R_6$, $R_7$ and $R_8$ are independently:
H,
$C_{1-4}$alkyl (e.g., methyl),
pyrid-2-yl substituted with hydroxy, or
—S(O)$_2$—NH$_2$;

(v) Provided that when X, Y and/or Z are N, then $R_6$, $R_7$ and/or $R_8$, respectively, are not present; and when X, Y and Z are all C, then at least one of $R_6$, $R_7$ or $R_8$ is —S(O)$_2$—NH$_2$ or pyrid-2-yl substituted with hydroxy, in free, pharmaceutically acceptable salt or prodrug form, including its enantiomers, diastereoisomers and racemates.

In one embodiment the invention provides administration of a PDE1 inhibitor for use in the methods of treatment and prophylaxis described herein, wherein the inhibitor is a compound according to the following:

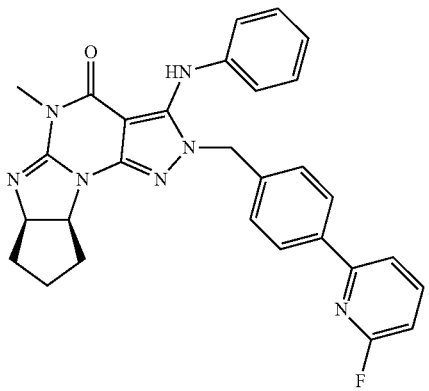 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

In still another embodiment, the invention provides administration of a PDE1 inhibitor for use in the methods of treatment and prophylaxis described herein, wherein the inhibitor is a compound according to the following:

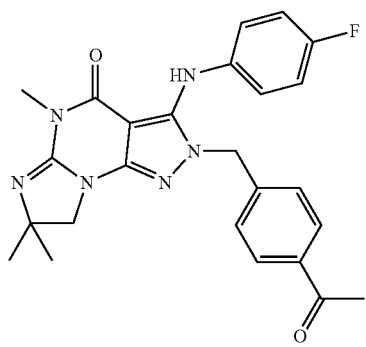 [SMILES: CC(=O)c1ccc(Cn2nc3c(c2Nc2ccc(F)cc2)C(=O)N(C)C2=NC(C)(C)CN23)cc1]

in free or pharmaceutically acceptable salt form.

In still another embodiment, the invention provides administration of a PDE1 inhibitor for use in the methods of treatment and prophylaxis described herein, wherein the inhibitor is a compound according to the following:

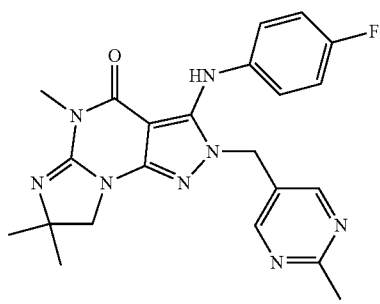 [SMILES: Cc1ncc(Cn2nc3c(c2Nc2ccc(F)cc2)C(=O)N(C)C2=NC(C)(C)CN23)cn1]

in free or pharmaceutically acceptable salt form.

In still another embodiment, the invention provides administration of a PDE1 inhibitor for use in the methods of treatment and prophylaxis described herein, wherein the inhibitor is a compound according to the following:

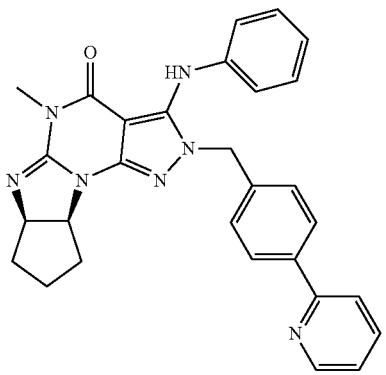 [SMILES: CN1C(=O)c2c(nn(Cc3ccc(-c4ccccn4)cc3)c2Nc2ccccc2)N2C1=N[C@@H]1CCC[C@@H]12]

in free or pharmaceutically acceptable salt form.

In one embodiment, selective PDE1 inhibitors of the any of the preceding formulae (e.g., Formula I, II, III and/or IV) are compounds that inhibit phosphodiesterase-mediated (e.g., PDE1-mediated, especially PDE1B-mediated) hydrolysis of cGMP and/or cAMP, e.g., the preferred compounds have an IC$_{50}$ of less than 1 μM, preferably less than 500 nM, preferably less than 50 nM, and preferably less than 5 nM in an immobilized-metal affinity particle reagent PDE assay, in free or salt form.

In other embodiments, the invention provides administration of a PDE1 inhibitor for use in the methods of treatment and prophylaxis described herein, wherein the PDE1 inhibitor is a compound according to the following:

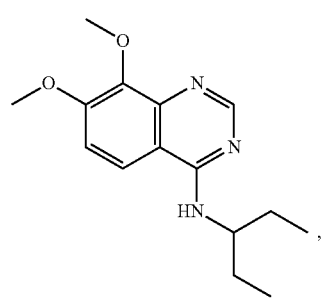

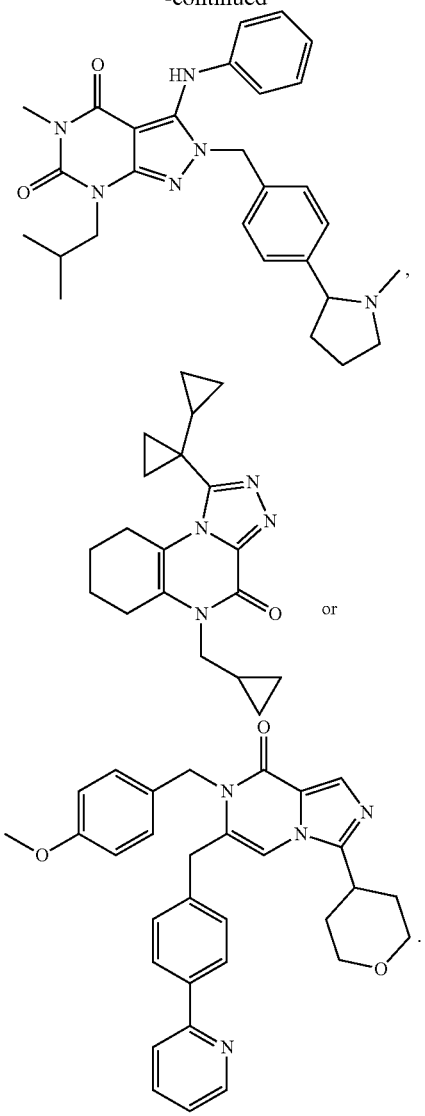

Further examples of PDE1 inhibitors suitable for use in the methods and treatments discussed herein can be found in International Publication WO2006133261A2; U.S. Pat. Nos. 8,273,750; 9,000,001; 9,624,230; International Publication WO2009075784A1; U.S. Pat. Nos. 8,273,751; 8,829,008; 9,403,836; International Publication WO2014151409A1, U.S. Pat. Nos. 9,073,936; 9,598,426; 9,556,186; U.S. Publication 2017/0231994A1, International Publication WO2016022893A1, and U.S. Publication 2017/0226117A1, each of which are incorporated by reference in their entirety.

Still further examples of PDE1 inhibitors suitable for use in the methods and treatments discussed herein can be found in International Publication WO2018007249A1; U.S. Publication 2018/0000786; International Publication WO2015118097A1; U.S. Pat. No. 9,718,832; International Publication WO2015091805A1; U.S. Pat. No. 9,701,665; U.S. Publication 2015/0175584A1; U.S. Publication 2017/0267664A1; International Publication WO2016055618A1; U.S. Publication 2017/0298072A1; International Publication WO2016170064A1; U.S. Publication 2016/0311831A1; International Publication WO2015150254A1; U.S. Publication 2017/0022186A1; International Publication WO2016174188A1; U.S. Publication 2016/0318939A1; U.S. Publication 2017/0291903A1; International Publication WO2018073251A1; International Publication WO2017178350A1; and U.S. Publication 2017/0291901A1; each of which are incorporated by reference in their entirety. In any situation in which the statements of any documents incorporated by reference contradict or are incompatible with any statements made in the present disclosure, the statements of the present disclosure shall be understood as controlling.

If not otherwise specified or clear from context, the following terms herein have the following meanings:

(a) "Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.

(b) "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy. Wherein the cycloalkyl optionally contains one or more atoms selected from N and O and/or S, said cycloalkyl may also be a heterocycloalkyl.

(c) "Heterocycloalkyl" is, unless otherwise indicated, saturated or unsaturated nonaromatic hydrocarbon moiety, preferably saturated, preferably comprising three to nine carbon atoms, at least some of which form a nonaromatic mono- or bicyclic, or bridged cyclic structure, wherein at least one carbon atom is replaced with N, O or S, which heterocycloalkyl may be optionally substituted, e.g., with halogen (e.g., chloro or fluoro), hydroxy, or carboxy.

(d) "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

(e) "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

(f) For ease of reference, the atoms on the pyrazolopyrimidine core of the Compounds of the Disclosure are numbered in accordance with the numbering depicted in Formula I, unless otherwise noted.

(g) It is intended that wherein the substituents end in "ene," for example, alkylene, phenylene or arylalkylene, said substitutents are intended to bridge or be connected to two other substituents. Therefore, methylene is intended to be —$CH_2$— and phenylene intended to be —$C_6H_4$— and arylalkylene is intended to be —$C_6H_4$—$CH_2$— or —$CH_2$—$C_6H_4$—.

Compounds of the Disclosure, e.g., substituted 4,5,7,8-tetrahydro-2H-imidazo[1,2-a]pyrrolo[3,4-e]pyrimidine or 4,5,7,8,9-pentahydro-2H-pyrimido[1,2-a]pyrrolo[3,4-e]pyrimidine, e.g., Compounds of Formula I, II, III or IV, may exist in free or salt form, e.g., as acid addition salts. In this specification unless otherwise indicated, language such as "Compounds of the Disclosure" is to be understood as embracing the compounds in any form, for example free or acid addition salt form, or where the compounds contain acidic substituents, in base addition salt form. The Compounds of the Disclosure are intended for use as pharmaceuticals, therefore pharmaceutically acceptable salts are preferred. Salts which are unsuitable for pharmaceutical uses may be useful, for example, for the isolation or purification of free Compounds of the Disclosure or their pharmaceutically acceptable salts, are therefore also included.

Compounds of the Disclosure, encompassing any of the compounds disclosed herein, e.g., optionally substituted 4,5,7,8-tetrahydro-(optionally 4-thioxo or 4-imino)-(1H or 2H)-imidazo[1,2-a]pyrazolo[4,3-e]pyrimidine or 4,5,7,8,9-pentahydro-(1H or 2H)-pyrimido[1,2-a]pyrazolo[4,3-e]pyrimidine compounds, e.g., (1 or 2 and/or 3 and/or 5)-substituted 4,5,7,8-tetrahydro-1H-imidazo[1,2-a]pyrazolo[4,3-e]pyrimidine, 4,5,7,8-tetrahydro-2H-imidazo[1,2-a]pyrazolo[4,3-e]pyrimidine, 4,5,7,8-tetrahydro-(1H or 2H)-pyrimido[1,2-a]pyrazolo[4,3-e]pyrimidine-4(5H)-imine, 7,8-dihydro-1H-imidazo[1,2-a]pyrazolo[4,3-e]pyrimidine-4(5H)-thione or 7,8-dihydro-2H-imidazo[1,2-a]pyrazolo[4,3-e]pyrimidine-4(5H)-thione compounds, e.g., Compounds of Formula III, or Compound of Formula IV as described herein, may exist in free or salt form, e.g., as acid addition salts.

Compounds of the Disclosure may in some cases also exist in prodrug form. A prodrug form is compound which converts in the body to a Compound of the Disclosure. For example, when the Compounds of the Disclosure contain hydroxy or carboxy substituents, these substituents may form physiologically hydrolysable and acceptable esters. As used herein, "physiologically hydrolysable and acceptable ester" means esters of Compounds of the Disclosure which are hydrolysable under physiological conditions to yield acids (in the case of Compounds of the Disclosure which have hydroxy substituents) or alcohols (in the case of Compounds of the Disclosure which have carboxy substituents) which are themselves physiologically tolerable at doses to be administered. Therefore, wherein the Compound of the Disclosure contains a hydroxy group, for example, Compound-OH, the acyl ester prodrug of such compound, i.e., Compound-O—C(O)—$C_{1-4}$alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Disclosure contains a carboxylic acid, for example, Compound—C(O)OH, the acid ester prodrug of such compound, Compound—C(O)O—$C_{1-4}$alkyl can hydrolyze to form Compound—C(O)OH and HO—$C_{1-4}$alkyl. As will be appreciated the term thus embraces conventional pharmaceutical prodrug forms.

In another embodiment, the disclosure further provides a pharmaceutical composition comprising a Compound of the Disclosure, in free or pharmaceutically acceptable salt form, in admixture with a pharmaceutically acceptable carrier.

In another embodiment, the disclosure further provides a pharmaceutical composition comprising a Compound of the Disclosure, in free, pharmaceutically acceptable salt or prodrug form, in admixture with a pharmaceutically acceptable carrier.

In some embodiments, the Compounds of the Disclosure may be modified to affect their rate of metabolism, e.g., to increase half life in vivo. In some embodiments, the compounds may be deuterated or fluorinated to reduce the rate of metabolism of the compounds disclosed herein.

In still another further embodiment, the compounds disclosed herein may be in the form of a pharmaceutical composition, for example for oral administration, e.g., in the form of tablets or capsules, or for parenteral administration. In some embodiments, the compounds are provided in the form of a long acting depot composition for administration by injection to provide sustained release. In some embodiments, the solid drug for oral administration or as a depot may be in a suitable polymer matrix to provide delayed release of the active compound.

The Compounds of the Disclosure and their pharmaceutically acceptable salts may be made using the methods as described and exemplified herein and by methods similar thereto and by methods known in the chemical art. If not commercially available, starting materials for these processes may be made by procedures, which are selected from the chemical art using techniques which are similar or analogous to the synthesis of known compounds. Starting materials and methods of making Compounds of the Disclosure are described in the patent applications cited and incorporated by reference above.

The Compounds of the Disclosure include their enantiomers, diastereoisomers and racemates, as well as their polymorphs, hydrates, solvates and complexes. Some individual compounds within the scope of this disclosure may contain double bonds. Representations of double bonds in this disclosure are meant to include both the E and the Z isomer of the double bond. In addition, some compounds within the scope of this disclosure may contain one or more asymmetric centers. This disclosure includes the use of any of the optically pure stereoisomers as well as any combination of stereoisomers.

It is also intended that the Compounds of the Disclosure encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Disclosure may be replaced with deuterium (a stable isotope which is non-raradioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species of I, C and F. Another example of useful isotope of the compound of the disclosure is the $^{11}C$ isotope. These radio isotopes are useful for radio-imaging and/or pharmacokinetic studies of the compounds of the disclosure.

Methods of using Compounds of the Disclosure

The compounds of the present disclosure are useful in the treatment of diseases characterized by disruption of or damage to cGMP/PKG and/or cAMP/PKA signaling mediated pathways, e.g., as a result of increased expression of PDE1 or decreased expression of cGMP/PKG or cAMP/PKA activity due to inhibition or reduced levels of inducers of cyclic nucleotide synthesis, such as dopamine and nitric oxide (NO). It is believed that by inhibiting PDE1, for example, that this action could reverse or prevent the attenuation of cGMP/PKG or cAMP/PKA signaling (e.g., enhance cGMP or cAMP, respectively). Therefore, administration or use of a preferred PDE1 inhibitor as described herein, e.g., a PDE1 inhibitor as hereinbefore described, e.g., a Compound of Formula I, II, III, IV, could provide a potential means to provide a treatment for various cardiovascular diseases and disorders.

The present disclosure provides methods of treatment of any one or more of the following conditions:
(i) Neurodegenerative diseases, including Parkinson's disease, restless leg, tremors, dyskinesias, Huntington's disease, Alzheimer's disease, and drug-induced movement disorders;
(ii) Mental disorders, including depression, attention deficit disorder, attention deficit hyperactivity disorder, bipolar illness, anxiety, sleep disorders, cognitive impairment, dementia, psychostimulant withdrawal, and drug addiction;
(iii) Circulatory and cardiovascular disorders, including cerebrovascular disease, stroke, congestive heart disease, hypertension, pulmonary hypertension, and sexual dysfunction;
(iv) Respiratory and inflammatory disorders, including asthma, chronic obstructive pulmonary disease, and allergic rhinitis, as well as autoimmune and inflammatory diseases; and/or
(v) Any disease or condition characterized by low levels of cAMP and/or cGMP (or inhibition of cAMP and/or cGMP signaling pathways) in cells expressing PDEL comprising administering an effective amount of a Compound of the Disclosure to a human or animal patient in need thereof.

In various embodiments, the present disclosure provides for a method [Method 1] of mitigating a side effect of a dopamine replacement therapy, the method comprising administering a pharmaceutically effective amount of a PDE1 inhibitor (e.g., a compound according to Formula I, II, III, or IV) to a subject in need thereof (e.g. a patient suffering from Parkinson's disease receiving dopamine replacement therapy). For example, the present disclosure provides for the following embodiments of Method 1:

1.1 Method 1, wherein the PDE1 inhibitor is one of Formula I, II, III, or IV, as hereinbefore described, in free or pharmaceutically acceptable salt form.

1.2 Any foregoing method wherein the PDE1 inhibitor comprises (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one:

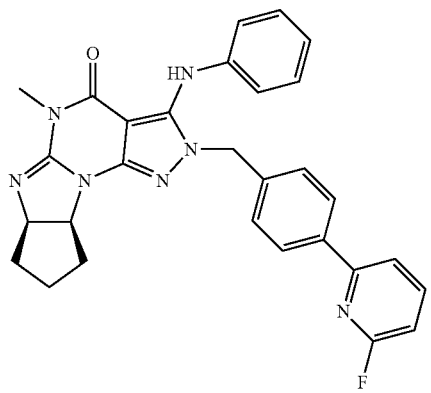 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

1.3 Any foregoing inhibitor wherein the PDE1 inhibitor comprises 7,8-dihydro-2-(4-acetylbenzyl)-3-(4-fluoro-phenylamino)-5,7,7-trimethyl-[2H]-imidazo-[1,2-a]pyrazolo[4,3-e]pyrimidin-4(5H)-one:

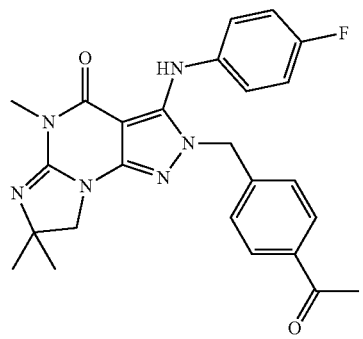 [SMILES: CC(=O)c1ccc(Cn2nc3c(c2Nc2ccc(F)cc2)C(=O)N(C)C2=NC(C)(C)CN23)cc1]

in free or pharmaceutically acceptable salt form.

1.4 Any foregoing therapy wherein the PDE1 inhibitor comprises 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one

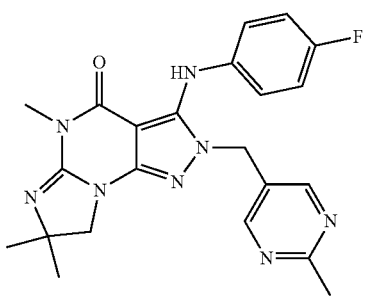 [SMILES: Cc1ncc(Cn2nc3c(c2Nc2ccc(F)cc2)C(=O)N(C)C2=NC(C)(C)CN23)cn1]

in free or pharmaceutically acceptable salt form.

1.5 Any foregoing method wherein the patient is a patient suffering from Parkinson's disease receiving dopamine replacement therapy.

1.6 Any of the preceding methods wherein the dopamine replacement therapy is selected from a dopamine precursor, e.g., levodopa (L-DOPA), dopamine agonists (DAs), and enzyme inhibitors selected from monoamine oxidase (MAO)-B inhibitors, catechol-O-methyltrasferase (COMT) inhibitors, and carbodopa.

1.7 Any of the preceding methods, wherein the dopamine replacement therapy comprises administration of a dopaminergic agonist.

1.8 Any preceding method wherein the dopamine replacement therapy comprises administration of levodopa.

1.9 Any of the preceding methods, wherein the dopamine replacement therapy is administered to treat Parkinson's disease, restless leg, tremors, dyskinesias, Huntington's disease, Alzheimer's disease, and drug-induced movement disorders; attention deficit disorder, attention deficit hyperactivity disorder, bipolar illness, cognitive impairment, dementia, and/or drug addiction; pulmonary hypertension; or chronic obstructive pulmonary disease.

1.10 Any of the preceding methods, wherein the dopamine replacement therapy is administered to treat Parkinson's Disease.

1.11 Any of the preceding methods, wherein the dopamine replacement therapy comprises administration of a dopaminergic agonist (e.g., levodopa (L-dopa), carbidopa, apomorphine, pramipexole, ropinirole, amantadine, rotigotine), anticholinergic agents (e.g., antipsychotics (e.g., clozapine, quetiapine), atropine, benztropine, benzotropine mesylate, biperiden, chlorpeniramine, citalopram, sertraline, dicyclomine, dimenhydrinate, diphenhydramine, doxepin, doxylamine, glycopyrrolate, glycopyrrolium, ipratropium, orphenadrine, oxitropium, oxybutynin, promethazine, propantheline bromide, tolterodine, tiotropium, tricyclic antidepressants, trihexyphenidyl, scopolamine, solifenacin, tropicamide), monoamine oxidase (MAO)-B inhibitors (isocarboxazid, nialamide, phenelzine, hydracarbazine, tranylcypromine, rasagiline, selegiline, safinamide), catechol-O-methyl transferase (COMT) inhibitors (e.g., entacapone, tolcapone, opicapone, nitecapone), antiparkinson agents (e.g., SSIAs (e.g., pimavanserin)), and combinations thereof.

1.12 Any of the preceding methods, wherein the dopamine replacement therapy comprises administration of a dopaminergic agonist selected from levodopa (L-dopa), carbidopa, apomorphine, pramipexole, ropinirole, amantadine, rotigotine, and combinations thereof.

1.13 Any of the preceding methods, wherein the dopamine replacement therapy comprises administration of an anticholinergic agent selected from antipsychotics (e.g., clozapine, quetiapine), atropine, benztropine, benzotropine mesylate, biperiden, chlorpeniramine, citalopram, sertraline, dicyclomine, dimenhydrinate, diphenhydramine, doxepin, doxylamine, glycopyrrolate, glycopyrrolium, ipratropium, orphenadrine, oxitropium, oxybutynin, promethazine, propantheline bromide, tolterodine, tiotropium, tricyclic antidepressants, trihexyphenidyl, scopolamine, solifenacin, tropicamide, and combinations thereof.

1.14 Any of the preceding methods, wherein the dopamine replacement therapy comprises administration of a monoamine oxidase (MAO)-B inhibitor selected from isocarboxazid, nialamide, phenelzine, hydracarbazine, tranylcypromine, rasagiline, selegiline, safinamide and combinations thereof.

1.15 The preceding method wherein the MAO-B inhibitor is a selective MAO-B inhibitor selected from rasagiline, selegiline, safinamide and combinations thereof.

1.16 Any of the preceding methods, wherein the dopamine replacement therapy comprises administration of a catechol-O-methyl transferase (COMT) inhibitor selected from entacapone, tolcapone, opicapone, nitecapone and combinations thereof.

1.17 Any of the preceding methods, wherein the dopamine replacement therapy comprises administration of an antiparkinsons agent selected from a selective serotonin inverse agonist (SSIA).

1.18 The preceding method, wherein the SSIA is pimavanserin.

1.19 Any of the preceding methods, wherein the side effects of the dopamine replacement therapy comprise motor impairment or dyskinesia.

1.20 Any of the preceding methods wherein the side effects of the dopamine replacement therapy comprise dyskinesia.

1.21 Any preceding method, wherein the side effects of dopamine replacement therapy comprise motor impairment or dyskinesia consequent to administration of levodopa.

1.22 Any of the preceding methods, wherein administering the PDE1 inhibitor reduces or eliminates the occurrence of the side effects of dopamine replacement therapy (i.e., motor impairment or dyskinesia).

1.23 Any of the preceding methods, wherein administration of the PDE1 inhibitor improves motor performance and reduces motor complications in the "On" state relative to placebo treatment as assessed by the Movement Disorder Society Unified Parkinson's Disease Rating Scale (MDS-UPDRS).

1.24 Any of the preceding methods, wherein administration of the PDE1 inhibitor reduces dyskinesia symptoms as measured by the Unified Dyskinesia Rating Score (UDysRS) and increases total "On" time and "On" time without dyskinsias as rated by subjects using the Hauser Patient Motor Diary.

1.25 Any of the preceding methods, wherein the subject is suffering from mild to moderate Parkinson's Disease.

1.26 Any of the preceding methods, wherein the subject is suffering from motor impairment and/or dyskinesias consequent to dopamine replacement therapy administered for the treatment of Parkinson's Disease.

1.27 Any of the preceding methods, wherein the subject is suffering from motor impairment and/or dyskinesias consequent to administration of a dopaminergic agonist (e.g., levodopa (L-dopa), carbidopa, apomorphine, pramipexole, ropinirole, amantadine, rotigotine), anticholinergic agents (e.g., antipsychotics (e.g., clozapine, quetiapine), atropine, benztropine, benzotropine mesylate, biperiden, chlorpeniramine, citalopram, sertraline, dicyclomine, dimenhydrinate, diphenhydramine, doxepin, doxylamine, glycopyrrolate, glycopyrrolium, ipratropium, orphenadrine, oxitropium, oxybutynin, promethazine, propantheline bromide, tolterodine, tiotropium, tricyclic antidepressants, trihexyphenidyl, scopolamine, solifenacin, tropicamide), monoamine oxidase (MAO)-B inhibitors (isocarboxazid, nialamide, phenelzine, hydracarbazine, tranylcypromine, rasagiline, selegiline, safinamide), catechol-O-methyl transferase (COMT) inhibitors (e.g., entacapone, tolcapone, opicapone, nitecapone), antiparkinson agents (e.g., SSIAs (e.g., pimavanserin)), or combinations thereof.

1.28 Any of the preceding methods, wherein the PDE1 inhibitor is administered at a concentration of 0.01 mg/kg to 100 mg/kg.

1.29 Any of the preceding methods wherein the patient is a human and the PDE1 inhibitor is administered at an oral daily dosage of 1-100 mg.

1.30 Any of the preceding methods, wherein the PDE1 inhibitor is administered once daily at a dosage of 1 mg, 3, mg, 10 mg, 30 mg, or 90 mg.

1.31 Any of the preceding methods, wherein the PDE1 inhibitor is administered orally.

1.32 Any of the preceding methods, wherein the PDE1 inhibitor is administered as a tablet or capsule.

1.33 Any of the preceding methods wherein the patient is a human, the PDE1 inhibitor is administered at an oral daily dosage of 1-90 mg, e.g., 1 mg, 3, mg, 10 mg, 30 mg, or 90 mg, and the PDE1 inhibitor is selected from
  a. (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3- e]pyrimidin-4(2H)-one, in free or pharmaceutically acceptable salt form, e.g., monophosphate salt form;

b. 7,8-dihydro-2-(4-acetylbenzyl)-3-(4-fluorophenylamino)-5,7,7-trimethyl-[2H]-imidazo-[1,2-a]pyrazolo[4,3-e]pyrimidin-4(5H)-one, in free or pharmaceutically acceptable salt form; and c. 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one, in free or pharmaceutically acceptable salt form.

The disclosure further provides a PDE1 inhibitor for use in a method of reducing the side effects of a dopamine replacement therapy in a subject in need thereof, e.g., for use in any of Methods 1, et seq.

The disclosure further provides the use of a PDE1 inhibitor in the manufacture of a medicament for reducing the side effects of a dopamine replacement therapy in a subject in need thereof, e.g., a medicament for use in any of Methods 1, et seq.

In various embodiments, the present disclosure provides for a method [Method 2] of enhancing the efficacy of a dopamine replacement therapy, the method comprising administering a pharmaceutically effective amount of a PDE1 inhibitor (i.e., a compound according to Formula I, II, III, or IV) to a patient in need thereof, comprising administration of an effective amount of a PDE1 inhibitor to a patient in need thereof. For example, the present disclosure provides for the following Methods:

2.1 Method 2, wherein the PDE1 inhibitor is one of Formula I, II, III, or IV, as hereinbefore described, in free or pharmaceutically acceptable salt form.

2.2 Method 2 or 2.1, wherein the PDE1 inhibitor is (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one:

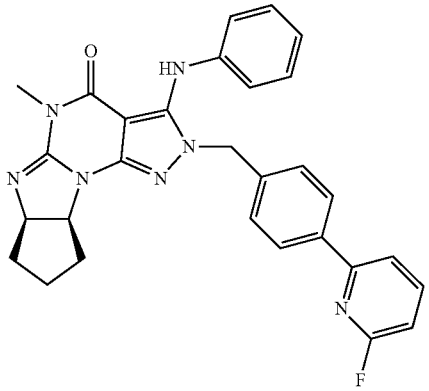 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

2.3 Method 2 or 2.1 wherein the PDE1 inhibitor is 7,8-dihydro-2-(4-acetylbenzyl)-3-(4-fluorophenylamino)-5,7,7-trimethyl-[2H]-imidazo-[1,2-a]pyrazolo[4,3-e]pyrimidin-4(5H)-one:

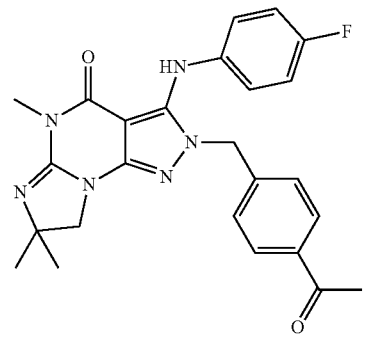 [SMILES: CC(=O)c1ccc(Cn2nc3c(c2Nc2ccc(F)cc2)C(=O)N(C)C2=NC(C)(C)CN23)cc1]

in free or pharmaceutically acceptable salt form.

2.4 Method 2 or 2.1 wherein the PDE1 inhibitor is 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one

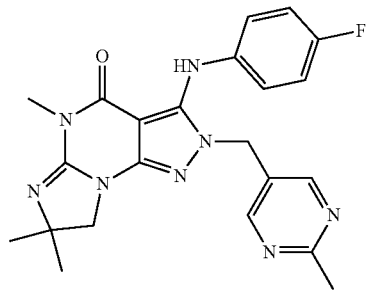 [SMILES: Cc1ncc(Cn2nc3c(c2Nc2ccc(F)cc2)C(=O)N(C)C2=NC(C)(C)CN23)cn1]

in free or pharmaceutically acceptable salt form.

2.5 Any of the preceding methods, wherein a dopaminergic agonist is administered as part of the dopamine replacement therapy.

2.6 Any of the preceding methods, wherein the dopamine replacement therapy is administered to treat Parkinson's disease, restless leg, tremors, dyskinesias, Huntington's disease, Alzheimer's disease, and drug-induced movement disorders; attention deficit disorder, attention deficit hyperactivity disorder, bipolar illness, cognitive impairment, dementia, and/or drug addiction; pulmonary hypertension; or chronic obstructive pulmonary disease.

2.7 Any of the preceding methods, wherein the dopamine replacement therapy is administered as part of a dopamine replacement therapy to treat Parkinson's Disease.

2.8 Any of the preceding methods, wherein the dopamine replacement therapy comprises administration of a dopaminergic agonist (e.g., levodopa (L-dopa), carbidopa, apomorphine, pramipexole, ropinirole, amantadine, rotigotine), anticholinergic agents (e.g., antipsychotics (e.g., clozapine, quetiapine), atropine, benztropine, benzotropine mesylate, biperiden, chlorpeniramine, citalopram, sertraline, dicyclomine, dimenhydrinate, diphenhydramine, doxepin, doxylamine, glycopyrrolate, glycopyrrolium, ipratropium, orphenadrine, oxitropium, oxybutynin, promethazine, propantheline bromide, tolterodine, tiotropium, tricyclic antidepressants, trihexyphenidyl, scopolamine, solifenacin, tropicamide), monoamine oxidase (MAO)-B inhibitors (isocarboxazid, nialamide, phenelzine, hydracarbazine, tranylcypromine, rasagiline, selegiline, safinamide), catechol-O-methyl transferase (COMT) inhibitors (e.g., entacapone, tolcapone, opicapone, nitecapone), antiparkinson agents (e.g., SSIAs (e.g., pimavanserin)), and combinations thereof.

2.9 Any of the preceding methods, wherein the dopamine replacement therapy comprises administration of a dopaminergic agonist selected from levodopa (L-dopa), carbidopa, apomorphine, pramipexole, ropinirole, amantadine, rotigotine, and combinations thereof.

2.10 Any of the preceding methods, wherein the dopamine replacement therapy comprises administration of an anticholinergic agent selected from antipsychotics (e.g., clozapine, quetiapine), atropine, benztropine, benzotropine mesylate, biperiden, chlorpeniramine, citalopram, sertraline, dicyclomine, dimenhydrinate, diphenhydramine, doxepin, doxylamine, glycopyrrolate, glycopyrrolium, ipratropium, orphenadrine, oxitropium, oxybutynin, promethazine, propantheline bromide, tolterodine, tiotropium, tricyclic antidepressants, trihexyphenidyl, scopolamine, solifenacin, tropicamide, and combinations thereof.

2.11 Any of the preceding methods, wherein the dopamine replacement therapy comprises administration of a monoamine oxidase (MAO)-B inhibitor selected from isocarboxazid, nialamide, phenelzine, hydracarbazine, tranylcypromine, rasagiline, selegiline, safinamide and combinations thereof.

2.12 Method 2.11, wherein the MAO-B inhibitor is a selective MAO-B inhibitor selected from rasagiline, selegiline, safinamide and combinations thereof.

2.13 Any of the preceding methods, wherein the dopamine replacement therapy comprises administration of a catechol-O-methyl transferase (COMT) inhibitor selected from entacapone, tolcapone, opicapone, nitecapone and combinations thereof.

2.14 Any of the preceding methods, wherein the dopamine replacement therapy comprises administration of an antiparkinsons agent selected from a selective serotonin inverse agonist (SSIA).

2.15 Method 2.14, wherein the SSIA is pimavanserin.

2.16 Any of the preceding methods, wherein the subject is suffering from mild to moderate Parkinson's Disease.

2.17 Any of the preceding methods, wherein the subject is suffering from motor impairment and/or dyskinesias consequent to dopamine replacement therapy.

2.18 Any of the preceding methods, wherein the subject is suffering from motor impairment and/or dyskinesias consequent to administration of a dopaminergic agonist (e.g., levodopa (L-dopa), carbidopa, apomorphine, pramipexole, ropinirole, amantadine, rotigotine), anticholinergic agents (e.g., antipsychotics (e.g., clozapine, quetiapine), atropine, benztropine, benzotropine mesylate, biperiden, chlorpeniramine, citalopram, sertraline, dicyclomine, dimenhydrinate, diphenhydramine, doxepin, doxylamine, glycopyrrolate, glycopyrrolium, ipratropium, orphenadrine, oxitropium, oxybutynin, promethazine, propantheline bromide, tolterodine, tiotropium, tricyclic antidepressants, trihexyphenidyl, scopolamine, solifenacin, tropicamide), monoamine oxidase (MAO)-B inhibitors (isocarboxazid, nialamide, phenelzine, hydracarbazine, tranylcypromine, rasagiline, selegiline, safinamide), catechol-O-methyl transferase (COMT) inhibitors (e.g., entacapone, tolcapone, opicapone, nitecapone), antiparkinson agents (e.g., SSIAs (e.g., pimavanserin)), or combinations thereof.

2.19 Any of the preceding methods, wherein the PDE1 inhibitor is administered at a concentration of 0.01 mg/kg to 100 mg/kg.

2.20 Any of the preceding methods wherein the patient is a human and the PDE1 inhibitor is administered at an oral daily dosage of 1-100 mg.

2.21 Any of the preceding methods, wherein the PDE1 inhibitor is administered once daily at a dosage of 1 mg, 3, mg, 10 mg, 30 mg, or 90 mg.

2.22 Any of the preceding methods, wherein the PDE1 inhibitor is administered orally.

2.23 Any of the preceding methods, wherein the PDE1 inhibitor is administered as a tablet or capsule.

2.24 Any of the preceding methods wherein the patient is a human, the PDE1 inhibitor is administered at an oral daily dosage of 1-90 mg, e.g., 1 mg, 3, mg, 10 mg, 30 mg, or 90 mg, and the PDE1 inhibitor is selected from
 a. (6aR,9aS)-5,6a,7,8,9,9a-hexahydro-5-methyl-3-(phenylamino)-2-((4-(6-fluoropyridin-2-yl)phenyl) methyl)-cyclopent[4,5]imidazo[1,2-a]pyrazolo[4,3-e]pyrimidin-4(2H)-one, in free or pharmaceutically acceptable salt form, e.g., monophosphate salt form;
 b. 7,8-dihydro-2-(4-acetylbenzyl)-3-(4-fluorophenylamino)-5,7,7-trimethyl-[2H]-imidazo-[1,2-a] pyrazolo[4,3-e]pyrimidin-4(5H)-one, in free or pharmaceutically acceptable salt form; and
 c. 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one, in free or pharmaceutically acceptable salt form.

The disclosure further provides a PDE1 inhibitor for use in a method of enhancing the efficacy of a dopamine replacement therapy, e.g., for use in any of Methods 2, et seq.

The disclosure further provides the use of a PDE1 inhibitor in the manufacture of a medicament for enhancing the efficacy of a dopamine replacement therapy, e.g., a medicament for use in any of Methods 2, et seq.

In various embodiments, the present disclosure provides for a method [Method 3] of treating a diseases or disorders associated with the dopamine D1 receptor intracellular pathway (e.g., Parkinson's disease), the method comprising administering a pharmaceutically effective amount of a PDE1 inhibitor (i.e., a compound according to Formula I, II, III, or IV) in combination with a dopamine replacement therapy to a subject in need thereof. For example, the present disclosure provides for the following Methods:

3.1 Method 3, wherein the PDE1 inhibitor is one of Formula I, II, III, or IV, as hereinbefore described, in free or pharmaceutically acceptable salt form.

3.2 Method 3 or 3.1, wherein the PDE1 inhibitor is (6aR,9aS)-5,6a,7,8,9,9a-hexahydro-5-methyl-3-(phenylamino)-2-((4-(6-fluoropyridin-2-yl)phenyl) methyl)-cyclopent[4,5]imidazo[1,2-a]pyrazolo[4,3-e] pyrimidin-4(2H)-one:

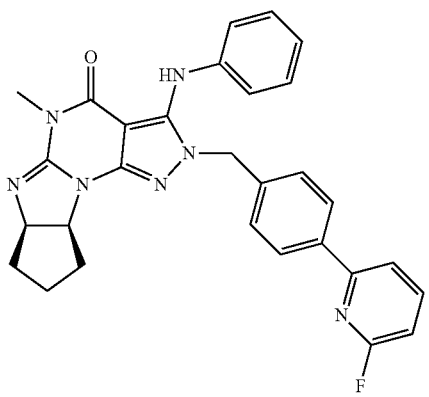 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

3.3 Method 3 or 3.1 wherein the PDE1 inhibitor is 7,8-dihydro-2-(4-acetylbenzyl)-3-(4-fluorophenylamino)-5,7,7-trimethyl-[2H]-imidazo-[1,2-a]pyrazolo[4,3-e]pyrimidin-4(5H)-one:

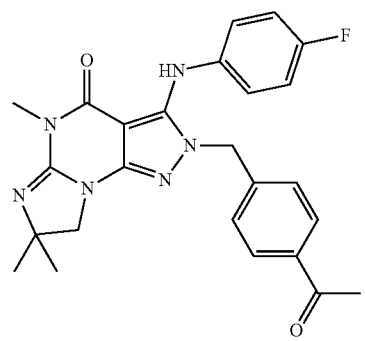 [SMILES: CC(=O)c1ccc(Cn2nc3c(c2Nc2ccc(F)cc2)C(=O)N(C)C2=NC(C)(C)CN23)cc1]

in free or pharmaceutically acceptable salt form.

3.4 Method 3 or 3.1 wherein the PDE1 inhibitor is 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one

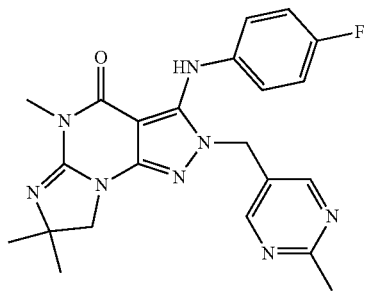 [SMILES: Cc1ncc(Cn2nc3c(c2Nc2ccc(F)cc2)C(=O)N(C)C2=NC(C)(C)CN23)cn1]

in free or pharmaceutically acceptable salt form.

3.5 Any of the preceding methods, wherein a dopaminergic agonist is administered as part of the dopamine replacement therapy.

3.6 Any of the preceding methods, wherein the dopamine replacement therapy is administered to treat Parkinson's disease, restless leg, tremors, dyskinesias, Huntington's disease, Alzheimer's disease, and drug-induced movement disorders; attention deficit disorder, attention deficit hyperactivity disorder, bipolar illness, cognitive impairment, dementia, and/or drug addiction; pulmonary hypertension; or chronic obstructive pulmonary disease.

3.7 Any of the preceding methods, wherein the dopamine replacement therapy is administered as part of a dopamine replacement therapy to treat Parkinson's Disease.

3.8 Any of the preceding methods, wherein the dopamine replacement therapy comprises administration of a dopaminergic agonist (e.g., levodopa (L-dopa), carbidopa, apomorphine, pramipexole, ropinirole, amantadine, rotigotine), anticholinergic agents (e.g., antipsychotics (e.g., clozapine, quetiapine), atropine, benztropine, benzotropine mesylate, biperiden, chlorpeniramine, citalopram, sertraline, dicyclomine, dimenhydrinate, diphenhydramine, doxepin, doxylamine, glycopyrrolate, glycopyrrolium, ipratropium, orphenadrine, oxitropium, oxybutynin, promethazine, propantheline bromide, tolterodine, tiotropium, tricyclic antidepressants, trihexyphenidyl, scopolamine, solifenacin, tropicamide), monoamine oxidase (MAO)-B inhibitors (isocarboxazid, nialamide, phenelzine, hydracarbazine, tranylcypromine, rasagiline, selegiline, safinamide), catechol-O-methyl transferase (COMT) inhibitors (e.g., entacapone, tolcapone, opicapone, nitecapone), antiparkinson agents (e.g., SSIAs (e.g., pimavanserin)), and combinations thereof.

3.9 Any of the preceding methods, wherein the dopamine replacement therapy comprises administration of a dopaminergic agonist selected from levodopa (L-dopa), carbidopa, apomorphine, pramipexole, ropinirole, amantadine, rotigotine, and combinations thereof.

3.10 Any of the preceding methods, wherein the dopamine replacement therapy comprises administration of an anticholinergic agent selected from antipsychotics (e.g., clozapine, quetiapine), atropine, benztropine, benzotropine mesylate, biperiden, chlorpeniramine, citalopram, sertraline, dicyclomine, dimenhydrinate, diphenhydramine, doxepin, doxylamine, glycopyrrolate, glycopyrrolium, ipratropium, orphenadrine, oxitropium, oxybutynin, promethazine, propantheline bromide, tolterodine, tiotropium, tricyclic antidepressants, trihexyphenidyl, scopolamine, solifenacin, tropicamide, and combinations thereof.

3.11 Any of the preceding methods, wherein the dopamine replacement therapy comprises administration of a monoamine oxidase (MAO)-B inhibitor selected from isocarboxazid, nialamide, phenelzine, hydracarbazine, tranylcypromine, rasagiline, selegiline, safinamide and combinations thereof.

3.12 Method 3.11, wherein the MAO-B inhibitor is a selective MAO-B inhibitor selected from rasagiline, selegiline, safinamide and combinations thereof.

3.13 Any of the preceding methods, wherein the dopamine replacement therapy comprises administration of a catechol-O-methyl transferase (COMT) inhibitor selected from entacapone, tolcapone, opicapone, nitecapone and combinations thereof.

3.14 Any of the preceding methods, wherein the dopamine replacement therapy comprises administration of an antiparkinsons agent selected from a selective serotonin inverse agonist (SSIA).

3.15 Method 3.14, wherein the SSIA is pimavanserin.

3.16 Any of the preceding methods, wherein the subject is suffering from mild to moderate Parkinson's Disease.

3.17 Any of the preceding methods, wherein the subject is suffering from motor impairment and/or dyskinesias consequent to dopamine replacement therapy.

3.18 Any of the preceding methods, wherein the subject is suffering from motor impairment and/or dyskinesias consequent to administration of a dopaminergic agonist (e.g., levodopa (L-dopa), carbidopa, apomorphine, pramipexole, ropinirole, amantadine, rotigotine), anticholinergic agents (e.g., antipsychotics (e.g., clozapine, quetiapine), atropine, benztropine, benzotropine mesylate, biperiden, chlorpeniramine, citalopram, sertraline, dicyclomine, dimenhydrinate, diphenhydramine, doxepin, doxylamine, glycopyrrolate, glycopyrrolium, ipratropium, orphenadrine, oxitropium, oxybutynin, promethazine, propantheline bromide, tolterodine, tiotropium, tricyclic antidepressants, trihexyphenidyl, scopolamine, solifenacin, tropicamide), monoamine oxidase (MAO)-B inhibitors (isocarboxazid, nialamide, phenelzine, hydracarbazine, tranylcypromine, rasagiline, selegiline, safinamide), catechol-O-methyl transferase (COMT) inhibitors (e.g., entacapone, tolcapone, opicapone, nitecapone), antiparkinson agents (e.g., SSIAs (e.g., pimavanserin)), or combinations thereof.

3.19 Any of the preceding methods, wherein the PDE1 inhibitor is administered at a concentration of 0.01 mg/kg to 100 mg/kg.

3.20 Any of the preceding methods wherein the patient is a human and the PDE1 inhibitor is administered at an oral daily dosage of 1-100 mg.

3.21 Any of the preceding methods, wherein the PDE1 inhibitor is administered once daily at a dosage of 1 mg, 3, mg, 10 mg, 30 mg, or 90 mg.

3.22 Any of the preceding methods, wherein the PDE1 inhibitor is administered orally.

3.23 Any of the preceding methods, wherein the PDE1 inhibitor is administered as a tablet or capsule.

3.24 Any of the preceding methods wherein the patient is a human, the PDE1 inhibitor is administered at an oral daily dosage of 1 mg, 3, mg, 10 mg, 30 mg, or 90 mg, and the PDE1 inhibitor is selected from
  a. (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one, in free or pharmaceutically acceptable salt form, e.g., monophosphate salt form;
  b. 7,8-dihydro-2-(4-acetylbenzyl)-3-(4-fluorophenylamino)-5,7,7-trimethyl-[2H]-imidazo-[1,2-a]pyrazolo[4,3-e]pyrimidin-4(5H)-one, in free or pharmaceutically acceptable salt form; and
  c. 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one, in free or pharmaceutically acceptable salt form.

The disclosure further provides a PDE1 inhibitor for use in a method for treating a diseases or disorders associated with the dopamine D1 receptor intracellular pathway (e.g., Parkinson's disease), e.g., for use in any of Methods 3, et seq.

The disclosure further provides the use of a PDE1 inhibitor in the manufacture of a medicament for treating a diseases or disorders associated with the dopamine D1 receptor intracellular pathway (e.g., Parkinson's disease), e.g., a medicament for use in any of Methods 3, et seq.

In various embodiments, the present disclosure provides for a method [Method 4] of enhancing cGMP and/or cAMP signaling in a subject suffering from dyskinesias and/or motor impairment, the method comprising administering a pharmaceutically effective amount of a PDE1 inhibitor (i.e., a compound according to Formula I, II, III, or IV) to a subject in need thereof. For example, the present disclosure provides for the following Methods:

4.1 Method 4, wherein the PDE1 inhibitor is one of Formula I, II, III, or IV, as hereinbefore described, in free or pharmaceutically acceptable salt form.

4.2 Method 4 or 4.1 wherein the PDE1 inhibitor is (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one:

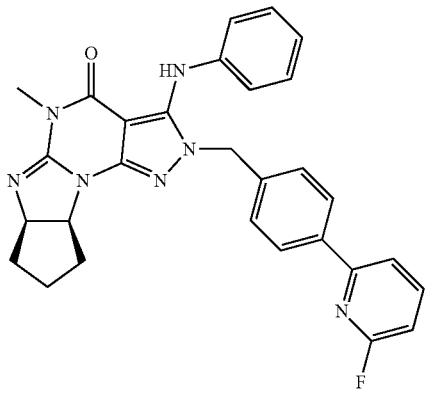 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

4.3 Method 4 or 4.1 wherein the PDE1 inhibitor is 7,8-dihydro-2-(4-acetylbenzyl)-3-(4-fluorophenylamino)-5,7,7-trimethyl-[2H]-imidazo-[1,2-a]pyrazolo[4,3-e]pyrimidin-4(5H)-one:

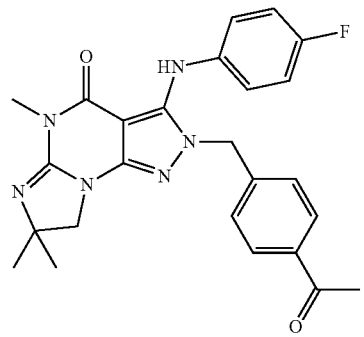 [SMILES: CC(=O)c1ccc(Cn2nc3c(c2Nc2ccc(F)cc2)C(=O)N(C)C2=NC(C)(C)CN23)cc1]

in free or pharmaceutically acceptable salt form.

4.4 Method 4 or 4.1 wherein the PDE1 inhibitor is 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one

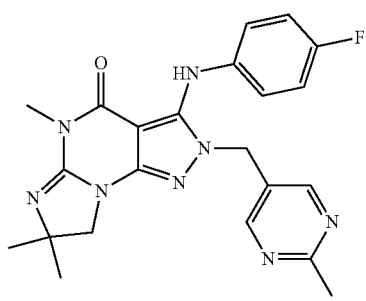 [SMILES: Cc1ncc(Cn2nc3c(c2Nc2ccc(F)cc2)C(=O)N(C)C2=NC(C)(C)CN23)cn1]

in free or pharmaceutically acceptable salt form.

4.5 Any of the preceding methods, wherein the dyskinesias and/or motor impairment are consequent to a dopamine replacement therapy administered to the subject.

4.6 Any of the preceding methods, wherein the subject is receiving a dopamine replacement therapy in the treatment of a a disease or disorder associated with the dopamine D1 receptor intracellular pathway (e.g., Parkinson's disease).

4.7 Methods 4.5-4.6, wherein a dopaminergic agonist is administered as part of the dopamine replacement therapy.

4.8 Any of Methods 4.5-4.7, wherein the dopamine replacement therapy is administered to treat Parkinson's disease, restless leg, tremors, dyskinesias, Huntington's disease, Alzheimer's disease, and drug-induced movement disorders; attention deficit disorder, attention deficit hyperactivity disorder, bipolar illness, cognitive impairment, dementia, and/or drug addiction; pulmonary hypertension; or chronic obstructive pulmonary disease.

4.9 Any of Methods 4.5-4.8, wherein the dopamine replacement therapy is administered as part of a dopamine replacement therapy to treat Parkinson's Disease.

4.10 Any of Methods 4.5-4.9, wherein the dopamine replacement therapy comprises administration of a dopaminergic agonist (e.g., levodopa (L-dopa), carbidopa, apomorphine, pramipexole, ropinirole, amantadine, rotigotine), anticholinergic agents (e.g., antipsychotics (e.g., clozapine, quetiapine), atropine, benztropine, benzotropine mesylate, biperiden, chlorpeniramine, citalopram, sertraline, dicyclomine, dimenhydrinate, diphenhydramine, doxepin, doxylamine, glycopyrrolate, glycopyrrolium, ipratropium, orphenadrine, oxitropium, oxybutynin, promethazine, propantheline bromide, tolterodine, tiotropium, tricyclic antidepressants, trihexyphenidyl, scopolamine, solifenacin, tropicamide), monoamine oxidase (MAO)-B inhibitors (isocarboxazid, nialamide, phenelzine, hydracarbazine, tranylcypromine, rasagiline, selegiline, safinamide), catechol-O-methyl transferase (COMT) inhibitors (e.g., entacapone, tolcapone, opicapone, nitecapone), antiparkinson agents (e.g., SSIAs (e.g., pimavanserin)), and combinations thereof.

4.11 Any of Methods 4.5-4.10, wherein the dopamine replacement therapy comprises administration of a dopaminergic agonist selected from levodopa (L-dopa), carbidopa, apomorphine, pramipexole, ropinirole, amantadine, rotigotine, and combinations thereof.

4.12 Any of Methods 4.5-4.11, wherein the dopamine replacement therapy comprises administration of an anticholinergic agent selected from antipsychotics (e.g., clozapine, quetiapine), atropine, benztropine, benzotropine mesylate, biperiden, chlorpeniramine, citalopram, sertraline, dicyclomine, dimenhydrinate, diphenhydramine, doxepin, doxylamine, glycopyrrolate, glycopyrrolium, ipratropium, orphenadrine, oxitropium, oxybutynin, promethazine, propantheline bromide, tolterodine, tiotropium, tricyclic antidepressants, trihexyphenidyl, scopolamine, solifenacin, tropicamide, and combinations thereof.

4.13 Any of Methods 4.5-4.12, wherein the dopamine replacement therapy comprises administration of a monoamine oxidase (MAO)-B inhibitor selected from isocarboxazid, nialamide, phenelzine, hydracarbazine, tranylcypromine, rasagiline, selegiline, safinamide and combinations thereof.

4.14 Method 1.13, wherein the MAO-B inhibitor is a selective MAO-B inhibitor selected from rasagiline, selegiline, safinamide and combinations thereof.

4.15 Any of Methods 4.5-4.14, wherein the dopamine replacement therapy comprises administration of a catechol-O-methyl transferase (COMT) inhibitor selected from entacapone, tolcapone, opicapone, nitecapone and combinations thereof.

4.16 Any of Methods 4.5-4.15, wherein the dopamine replacement therapy comprises administration of an antiparkinsons agent selected from a selective serotonin inverse agonist (SSIA).

4.17 Method 1.16, wherein the SSIA is pimavanserin.

4.18 Any of Methods 4.5-4.17, wherein the subject was receiving the dopamine replacement therapy prior to occurrence of the motor impairment or dyskinesia.

4.19 Any of Methods 4.5-4.18, wherein the subject was receiving the dopamine replacement therapy prior to administration of the PDE1 inhibitor.

4.20 Any of Methods 4.5-4.19, wherein the motor impairment or dyskinesia are side effects of the dopamine replacement therapy.

4.21 Any of the preceding methods, wherein administering the PDE1 inhibitor reduces or eliminates the occurrence of the motor impairment or dyskinesia.

4.22 Any of the preceding methods, wherein administration of the PDE1 inhibitor improves motor performance and reduces motor complications in the "On" state relative to placebo treatment as assessed by the Movement Disorder Society Unified Parkinson's Disease Rating Scale (MDS-UPDRS).

4.23 Any of the preceding methods, wherein administration of the PDE1 inhibitor reduces dyskinesia symptoms as measured by the Unified Dyskinesia Rating Score (UDysRS) and increases total "On" time and "On" time without dyskinsias as rated by subjects using the Hauser Patient Motor Diary.

4.24 Any of the preceding methods, wherein the subject is suffering from mild to moderate Parkinson's Disease.

4.25 Any of the preceding methods, wherein the subject is suffering from motor impairment and/or dyskinesias consequent to dopamine replacement therapy.

4.26 Any of the preceding methods, wherein the subject is suffering from motor impairment and/or dyskinesias consequent to administration of a dopaminergic agonist (e.g., levodopa (L-dopa), carbidopa, apomorphine, pramipexole, ropinirole, amantadine, rotigotine), anticholinergic agents (e.g., antipsychotics (e.g., clozapine, quetiapine), atropine, benztropine, benzotropine mesylate, biperiden, chlorpeniramine, citalopram, sertraline, dicyclomine, dimenhydrinate, diphenhydramine, doxepin, doxylamine, glycopyrrolate, glycopyrrolium, ipratropium, orphenadrine, oxitropium, oxybutynin, promethazine, propantheline bromide, tolterodine, tiotropium, tricyclic antidepressants, trihexyphenidyl, scopolamine, solifenacin, tropicamide), monoamine oxidase (MAO)-B inhibitors (isocarboxazid, nialamide, phenelzine, hydracarbazine, tranylcypromine, rasagiline, selegiline, safinamide), catechol-O-methyl transferase (COMT) inhibitors (e.g., entacapone, tolcapone, opicapone, nitecapone), antiparkinson agents (e.g., SSIAs (e.g., pimavanserin)), or combinations thereof.

4.27 Any of the preceding methods, wherein the PDE1 inhibitor is administered at a concentration of 0.01 mg/kg to 100 mg/kg.

4.28 Any of the preceding methods wherein the patient is a human and the PDE1 inhibitor is administered at an oral daily dosage of 1-100 mg.

4.29 Any of the preceding methods, wherein the PDE1 inhibitor is administered once daily at a dosage of 1 mg, 3, mg, 10 mg, 30 mg, or 90 mg.

4.30 Any of the preceding methods, wherein the PDE1 inhibitor is administered orally.

4.31 Any of the preceding methods, wherein the PDE1 inhibitor is administered as a tablet or capsule.

4.32 Any of the preceding methods wherein the patient is a human, the PDE1 inhibitor is administered at an oral daily dosage of 1 mg, 3, mg, 10 mg, 30 mg, or 90 mg, and the PDE1 inhibitor is selected from
   a.  (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one, in free or pharmaceutically acceptable salt form, e.g., monophosphate salt form;
   b.  7,8-dihydro-2-(4-acetylbenzyl)-3-(4-fluorophenylamino)-5,7,7-trimethyl-[2H]-imidazo-[1,2-a] pyrazolo[4,3-e]pyrimidin-4(5H)-one, in free or pharmaceutically acceptable salt form; and
   c.  3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one, in free or pharmaceutically acceptable salt form.

The disclosure further provides a PDE1 inhibitor for use in a method of enhancing cGMP and/or cAMP signaling in a subject suffering from dyskinesias and/or motor impairment, e.g., for use in any of Methods 4, et seq.

The disclosure further provides the use of a PDE1 inhibitor in the manufacture of a medicament of enhancing cGMP and/or cAMP signaling in a subject suffering from dyskinesias and/or motor impairment, e.g., a medicament for use in any of Methods 4, et seq.

Combination Therapies with PDE1 Inhibitors

In some embodiments, the PDE1 inhibitor is administered in combination with other therapeutic modalities. Thus, in addition to the therapies described above, one may also provide to the patient more pharmaceutical cardiac therapies. Examples of other therapies include, without limitation, dopaminergic agonists, anticholinergic agents, monoamine oxidase (MAO)-B inhibitors, catechol-O-methyl transferase (COMT) inhibitors, antiparkinson agents, and combinations thereof. A particular form of combination therapy will include the use of PDE1 inhibitors.

Combinations may be achieved by administering a single composition or pharmacological formulation that includes the PDE1 inhibitor and one or more additional therapeutic agents, or by administration of two distinct compositions or formulations, separately, simultaneously or sequentially, wherein one composition includes the PDE1 inhibitor and the other includes the additional therapeutic agent or agents. The therapy using a PDE1 inhibitor may precede or follow administration of the other agent(s) by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In some embodiments, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a PDE1 inhibitor, or an additional therapeutic agent will be desired. In this regard, various combinations may be employed. By way of illustration, where the PDE1 inhibitor is "A" and the additional therapeutic agent is "B," the following permutations based on 3 and 4 total administrations are exemplary:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Non-limiting examples of a dopamine replacement therapy that may be used in the present invention include a dopaminergic agonist, anticholinergic agents, monoamine oxidase (MAO)-B inhibitors, catechol-O-methyl transferase (COMT) inhibitors, antiparkinson agents, and combinations thereof. Other combinations are likewise contemplated. Some specific agents are described below.

Dopaminergic agonists may refer to any pharmaceutical agent which directly stimulates postsynaptic dopamine receptors to provide therapeutic benefit. Nonlimiting examples of dopaminergic agonists include levodopa (L-dopa), carbidopa, apomorphine, pramipexole, ropinirole, amantadine, rotigotine, and combinations thereof.

Anticholinergic agents may refer to any pharmaceutical agent that antagonizes acetylcholine in the central or peripheral nervous system. Nonlimiting examples of anticholinergic agents include antipsychotics (e.g., clozapine, quetiapine), atropine, benztropine, benzotropine mesylate, biperiden, chlorpeniramine, citalopram, sertraline, dicyclomine, dimenhydrinate, diphenhydramine, doxepin, doxylamine, glycopyrrolate, glycopyrrolium, ipratropium, orphenadrine, oxitropium, oxybutynin, promethazine, propantheline bromide, tolterodine, tiotropium, tricyclic antidepressants, trihexyphenidyl, scopolamine, solifenacin, tropicamide, and combinations thereof. Treatments may also include acetylcholinesterase inhibitors such as donepezil, rivastigmine, galantamine, and combinations thereof.

Monoamine oxidase inhibitors may refer to a drug that inhibits the activity of MAO-B oxidases responsible for inactivating dopamine. As referred herein, the monoamine oxidase inhibitors may be nonselective or selective MAO-B inhibitors. Nonlimiting examples of nonselective monoamine oxidase inhibitors include isocarboxazid, nialamide, phenelzine, hydracarbazine, tranylcypromine, and combinations thereof. Nonlimiting examples of selective MAO-B inhibitors include rasagiline, selegiline, safinamide, and combinationas thereof.

Catechol-O-methyl transferase (COMT) inhibitors refers to a drug that inhibits the peripheral metabolism of levodopa. Nonlimiting examples of COMT inhibitors include entacapone, tolcapone, opicapone, nitecapone and combinations thereof.

Antiparkinson agents refers broadly to any pharmaceutical agent useful in the treatment of Parkinson's Disease. Nonlimiting examples of an antiparkinson agent include selective serotonin inverse agonists, such as pimavanserin.

Accordingly, in various embodiments, the present disclosure also provides for a pharmaceutical combination [Combination 1] therapy comprising a pharmaceutically effective amount of a PDE1 inhibitor (e.g., a compound according to Formula I, II, III, or IV) and a dopamine replacement therapy (e.g., dopaminergic agonist), for administration in a method of reducing the side effects of a dopamine replacement therapy e.g., in accordance with any of Method 1, et seq., or for enhancing the efficacy of the dopamine replacement therapy, e.g. in accordance with any of Method 2, et seq., or for treating a diseases or disorders associated with the dopamine D1 receptor intracellular pathway (e.g., Parkinson's disease), e.g., in accordance with any of Method 3, et seq., or for enhancing cGMP and/or cAMP signaling in a subject suffering from dyskinesias and/or motor impairment, e.g., in accordance with any of Method 4, et seq. For example, the present disclosure provides for the following Combinations:

1.1 Combination 1 wherein the PDE1 inhibitor and the dopamine replacement therapy are in a single dosage form, e.g., a tablet or capsule, in combination or association with a pharmaceutically acceptable diluent or carrier.

1.2 Combination 1 wherein the PDE1 inhibitor and the dopamine replacement therapy are in a single package, e.g., with instructions for administration simultaneously or sequentially.

1.3 Any of the preceding combinations, wherein the PDE1 inhibitor is one of Formula I, II, III, or IV, in free or pharmaceutically acceptable salt form.

1.4 Any of the preceding combinations wherein the PDE1 inhibitor is selected from
  a. (6aR,9aS)-5,6a,7,8,9,9a-hexahydro-5-methyl-3-(phenylamino)-2-((4-(6-fluoropyridin-2-yl)phenyl)methyl)-cyclopent[4,5]imidazo[1,2-a]pyrazolo[4,3-e]pyrimidin-4(2H)-one, in free or pharmaceutically acceptable salt form, e.g., monophosphate salt form;
  b. 7,8-dihydro-2-(4-acetylbenzyl)-3-(4-fluorophenylamino)-5,7,7-trimethyl-[2H]-imidazo-[1,2-a]pyrazolo[4,3-e]pyrimidin-4(5H)-one, in free or pharmaceutically acceptable salt form; and
  c. 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one.

1.5 Any of the preceding combinations, wherein the dopamine replacement therapy comprises administration of a dopaminergic agonist (e.g., levodopa (L-dopa), carbidopa, apomorphine, pramipexole, ropinirole, amantadine, rotigotine), anticholinergic agents (e.g., antipsychotics (e.g., clozapine, quetiapine), atropine, benztropine, benzotropine mesylate, biperiden, chlorpeniramine, citalopram, sertraline, dicyclomine, dimenhydrinate, diphenhydramine, doxepin, doxylamine, glycopyrrolate, glycopyrrolium, ipratropium, orphenadrine, oxitropium, oxybutynin, promethazine, propantheline bromide, tolterodine, tiotropium, tricyclic antidepressants, trihexyphenidyl, scopolamine, solifenacin, tropicamide), monoamine oxidase (MAO)-B inhibitors (isocarboxazid, nialamide, phenelzine, hydracarbazine, tranylcypromine, rasagiline, selegiline, safinamide), catechol-O-methyl transferase (COMT) inhibitors (e.g., entacapone, tolcapone, opicapone, nitecapone), antiparkinson agents (e.g., SSIAs (e.g., pimavanserin)), and combinations thereof.

1.6 Any of the preceding combinations, wherein the dopamine replacement therapy comprises administration of a dopaminergic agonist selected from levodopa (L-dopa), carbidopa, apomorphine, pramipexole, ropinirole, amantadine, rotigotine, and combinations thereof.

1.7 Any of the preceding combinations, wherein the dopamine replacement therapy comprises administration of an anticholinergic agent selected from antipsychotics (e.g., clozapine, quetiapine), atropine, benztropine, benzotropine mesylate, biperiden, chlorpeniramine, citalopram, sertraline, dicyclomine, dimenhydrinate, diphenhydramine, doxepin, doxylamine, glycopyrrolate, glycopyrrolium, ipratropium, orphenadrine, oxitropium, oxybutynin, promethazine, propantheline bromide, tolterodine, tiotropium, tricyclic antidepressants, trihexyphenidyl, scopolamine, solifenacin, tropicamide, and combinations thereof.

1.8 Any of the preceding combinations, wherein the dopamine replacement therapy comprises administration of a monoamine oxidase (MAO)-B inhibitor selected from isocarboxazid, nialamide, phenelzine, hydracarbazine, tranylcypromine, rasagiline, selegiline, safinamide and combinations thereof.

1.9 Combination 1.8, wherein the MAO-B inhibitor is a selective MAO-B inhibitor selected from rasagiline, selegiline, safinamide and combinations thereof.

1.10 Any of the preceding combinations, wherein the dopamine replacement therapy comprises administration of a catechol-O-methyl transferase (COMT) inhibitor selected from entacapone, tolcapone, opicapone, nitecapone and combinations thereof.

1.11 Any of the preceding combinations, wherein the dopamine replacement therapy comprises administration of an antiparkinsons agent selected from a selective serotonin inverse agonist (SSIA).

1.12 Combination 1.11, wherein the SSIA is pimavanserin.

1.13 Any of the preceding combinations, wherein the subject was receiving the dopamine replacement therapy prior to administration of the PDE1 inhibitor.

1.14 Any of the preceding combinations, wherein the dopamine replacement therapy results in motor impairment or dyskinesia manifestations in the subject.

1.15 Combination 1.14, wherein administering the PDE1 inhibitor reduces or eliminates the occurrence of the motor impairment or dyskinesia.

1.16 Combinations 1.14-1.15, wherein administration of the PDE1 inhibitor improves motor performance and reduces motor complications in the "On" state relative to placebo treatment as assessed by the Movement Disorder Society Unified Parkinson's Disease Rating Scale (MDS-UPDRS).

1.17 Combinations 1.14-1.15, wherein administration of the PDE1 inhibitor reduces dyskinesia symptoms as measured by the Unified Dyskinesia Rating Score (UDysRS) and increases total "On" time and "On" time without dyskinsias as rated by subjects using the Hauser Patient Motor Diary.

1.18 Any of the preceding combinations, wherein the subject is suffering from mild to moderate Parkinson's Disease.

1.19 Any of the preceding combinations, wherein the subject is suffering from motor impairment and/or dyskinesias consequent to dopamine replacement therapy.

1.20 Any of the preceding combinations, wherein the subject is suffering from motor impairment and/or dyskinesias consequent to administration of a dopaminergic agonist (e.g., levodopa (L-dopa), carbidopa, apomorphine, pramipexole, ropinirole, amantadine, rotigotine), anticholinergic agents (e.g., antipsychotics (e.g., clozapine, quetiapine), atropine, benztropine, benzotropine mesylate, biperiden, chlorpeniramine, citalopram, sertraline, dicyclomine, dimenhydrinate, diphenhydramine, doxepin, doxylamine, glycopyrrolate, glycopyrrolium, ipratropium, orphenadrine, oxitropium, oxybutynin, promethazine, propantheline bromide, tolterodine, tiotropium, tricyclic antidepressants, trihexyphenidyl, scopolamine, solifenacin, tropicamide), monoamine oxidase (MAO)-B inhibitors (isocarboxazid, nialamide, phenelzine, hydracarbazine, tranylcypromine, rasagiline, selegiline, safinamide), catechol-O-methyl transferase (COMT) inhibitors (e.g., entacapone, tolcapone, opicapone, nitecapone), antiparkinson agents (e.g., SSIAs (e.g., pimavanserin)), or combinations thereof.

"PDE1 inhibitor" as used herein describes a compound(s) which selectively inhibit phosphodiesterase-mediated (e.g., PDE1-mediated, especially PDE1B-mediated) hydrolysis of cGMP, e.g., with an $IC_{50}$ of less than 1 μM, preferably less than 750 nM, more preferably less than 500 nM, more preferably less than 50 nM in an immobilized-metal affinity particle reagent PDE assay.

The phrase "Compounds of the Disclosure" or "PDE 1 inhibitors of the Disclosure", or like terms, encompasses any and all of the compounds disclosed herewith, e.g., a Compound of Formula I, Formula II, Formula III, Formula IV, Formula V, Formula VI, Formula VII, Formula VIII, Formula IX, Formula X, or Formula XI.

The words "treatment" and "treating" are to be understood accordingly as embracing prophylaxis and treatment or amelioration of symptoms of disease as well as treatment of the cause of the disease.

For methods of treatment, the word "effective amount" is intended to encompass a therapeutically effective amount to treat a specific disease or disorder.

The term "precondition" as used herein is intended to refer to treatment of cardiac tissue to produce resistance to the loss of blood supply or to oxygen. Ischemic preconditioning is an intrinsic process whereby repeated short episodes of ischemia protect the myocardium against a subsequent ischemic insult.

The terms "patient" or "subject" includes human or non-human (i.e., animal) patient. In particular embodiment, the disclosure encompasses both human and nonhuman. In another embodiment, the disclosure encompasses nonhuman. In other embodiment, the term encompasses human.

The term "comprising" as used in this disclosure is intended to be open-ended and does not exclude additional, unrecited elements or method steps.

The term "dyskinesia" as used herein, unless otherwise indicated, means any abnormal or uncontrollable movement including, but not limited to, chorea, tremor, ballism, dystonia, athetosis, myoclonus and tic.

The term or phrase "dopamine replacement therapy" or "dopaminergic agonist" or "dopamine agonist" as used herein, unless otherwise indicated, means any therapy that increases dopamine receptor stimulation, including, but not limited to, therapies that directly stimulate dopamine receptors (such as bromocriptine) and therapies that increase the levels of dopamine (such as L-dopa or drugs which inhibit dopamine metabolism). Dopamine replacement therapies include, but are not limited to, therapies comprising the administration of one or more of the following agents: L-dopa, L-dopa in combination with an L-dopa decarboxylase inhibitor such as carbidopa or benserazide, bromocriptine, dihydroergocryptine, etisulergine, AF-14, alaptide, pergolide, piribedil, dopamine D1 receptor agonists such as A-68939, A-77636, dihydrexine, and SKF-38393; dopamine D2 receptor agonists such as carbergoline, lisuride, N-0434, naxagolide, PD-118440, pramipexole, quinpirole and ropinirole; dopamine/β-adrenergic receptor agonists such as DPDMS and dopexamine; dopamine/5-HT uptake inhibitor/5-HT-1A agonists such as roxindole; dopamine/opiate receptor agonists such as NIH-10494; α2-adrenergic antagonist/dopamine agonists such as terguride; α2-adrenergic antagonist/dopamine D2 agonists such as ergolines and talipexole; dopamine uptake inhibitors such as GBR-12909, GBR-13069, GYKI-52895, and NS-2141; monoamine oxidase-B inhibitors such as selegiline, N-(2-butyl)-N-methylpropargylamine, N-methyl-N-(2-pentyl)propargylamine, AGN-1133, ergot derivatives, lazabemide, LU-53439, MD-280040 and mofegiline; and COMT inhibitors such as CGP-28014, entacapone and tolcapone. Dopamine replacement therapy, as referred to in the present invention, is used in the treatment of a central nervous system disorder such as, but not limited to, Parkinson's disease.

Compounds of the Disclosure, e.g., Formula I, II, III, and IV as hereinbefore described, in free or pharmaceutically acceptable salt form, may be used as a sole therapeutic agent, but may also be used in combination or for coadministration with other active agents.

Dosages employed in practicing the present disclosure will of course vary depending, e.g. on the particular disease or condition to be treated, the particular Compound of the Disclosure used, the mode of administration, and the therapy desired. Compounds of the Disclosure may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Disclosure, together with a pharmaceutically acceptable diluent or carrier therefor.

Pharmaceutical compositions comprising Compounds of the Disclosure may be prepared using conventional diluents or excipients and techniques known in the galenic art. Thus, oral dosage forms may include tablets, capsules, solutions, suspensions and the like.

EXAMPLES

Example 1

Evaluation of Compound 1 in the Treatment of Parkinson's Disease

A Phase 1/2 randomized, double-blind, placebo-controlled, multiple rising dose clinical study was carried out to evaluate Compound 1 (below) in patients with mild to moderate Parkinson's Disease (PD).

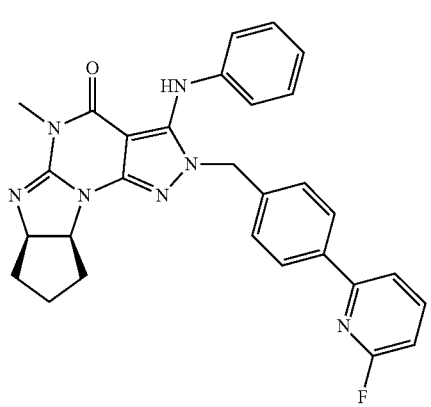

Compound 1

Compound 1 is administered in the form of the monophosphate salt.

The study is designed to evaluate the safety and tolerability of Compound 1 in patients who are maintained on stable PD therapy. Another objective is to evaluate the pharmacokinetic profile of Compound 1 and explore its potential utility to control motor fluctuations and to evaluate treatment of non-motor symptoms (e.g., daytime sleepiness, dysautonomia) associated with PD. Biomarkers of disease progression (i.e., inflammation) are assessed.

Inhibitors of PDE1 enhance intracellular signaling by preventing breakdown of cyclic nucleotides (cAMP, cGMP). Preclinical studies have shown that PDE1 inhibitors potentiate the positive effects of L-DOPA on motor performance. In this trial, once-daily oral administration of Compound 1 for 7 days, with no titration, is shown to have a favorable safety profile and was generally well tolerated across a broad range of doses from 1 mg to 90 mg. No serious adverse events are reported in the trial, and no clinically significant effects of Compound 1 compared to placebo are observed on vital signs, or cardiovascular or laboratory parameters. Clinical signs consistent with reductions in motor symptoms (UPDRS Part III) and motor complications on several rater-based and subject-based scales (UPDRS Part IV (data not shown), UDysRS and CISI-PD) were evident. Compound 1 increases on-time without causing dyskinesia (Hauser Diary). It is very surprising that while improving the effects of dopamine replacement therapies on motor symptoms, Compound 1 also reduces the side effects of these therapies.

40 patients with idiopathic PD are recruited for the study. Patients with mild to moderate PD (Hoehn and Yahr staging score of 1-3 assessed in the "On" state) maintained on stable PD therapy are randomly assigned to placebo or 5 cohorts of Compound 1 at 1 mg, 3 mg, 10 mg, 30 mg, and 90 mg administered orally once daily for 7 days. All patients participating in the study are maintained on their stable PD therapy (e.g., dopamine replacement therapies), some of which are taking more than one category of PD therapy. Of the 40 patients, there are 28 receiving carbidopa/L-dopa, 14 receiving a dopamine agonist, 5 receiving amantadine, and 3 receiving MAO inhibitors. No serious adverse events are reported in the trial, and no clinically significant effects of Compound 1 compared to placebo are observed on vital signs, and cardiovascular or laboratory parameters. The results show that Compound 1 did not induce or worsen motor complications in PD patients receiving concomitant dopamine replacement therapies.

Compound 1 exhibits linear pharmacokinetics for both the parent drug and metabolites across this broad dose range. Plasma steady state is achieved in the first 48 hours and supports once-a-day dosing for future efficacy trials.

Figure 2:
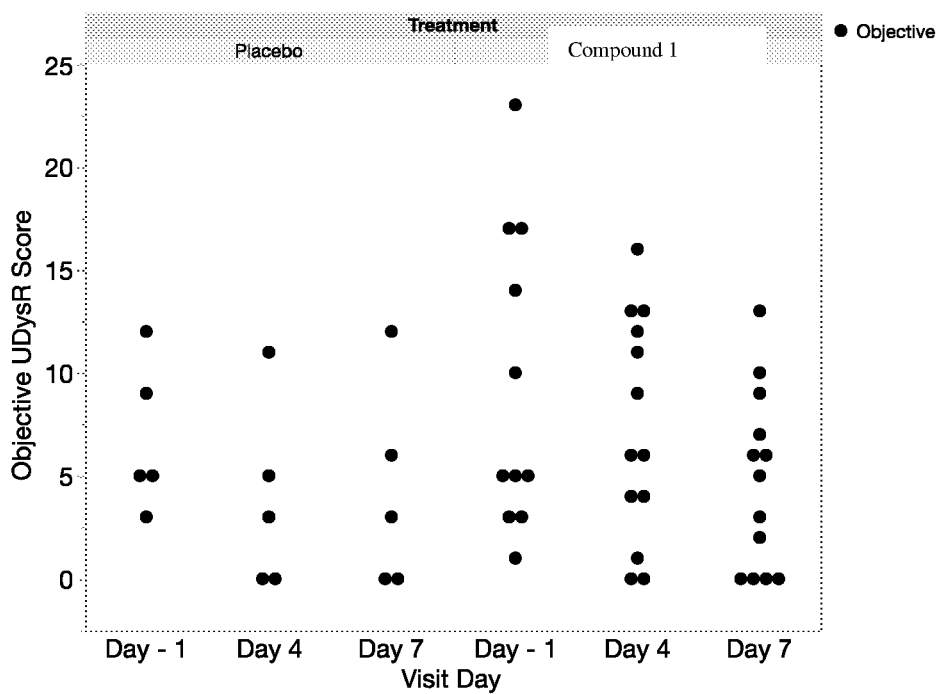
FIG. 2 shows the effect Compound 1 had on patients in UDysRS (Unified Dyskinesia Rating Scale) testing. Objective UDysRS Total Score Improves after Compound 1 treatment in subjects with dyskinesia at baseline.
Figure 3:
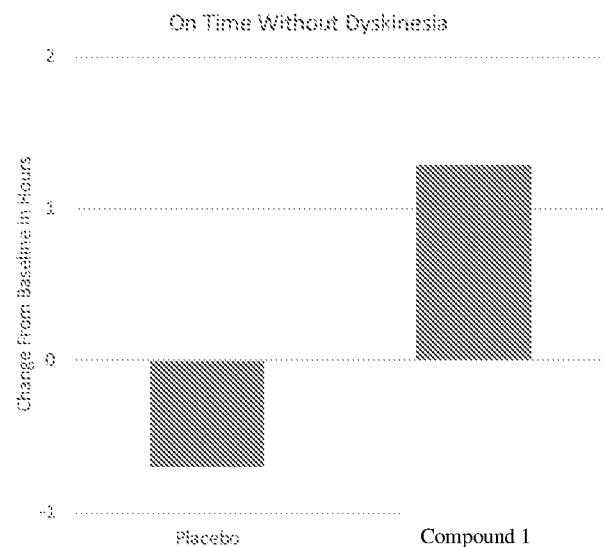
FIG. 3 shows that administration of Compound 1 increased "On" time without dyskinesias using the Hauser Patient Motor Diary versus placebo.
Figure 4:
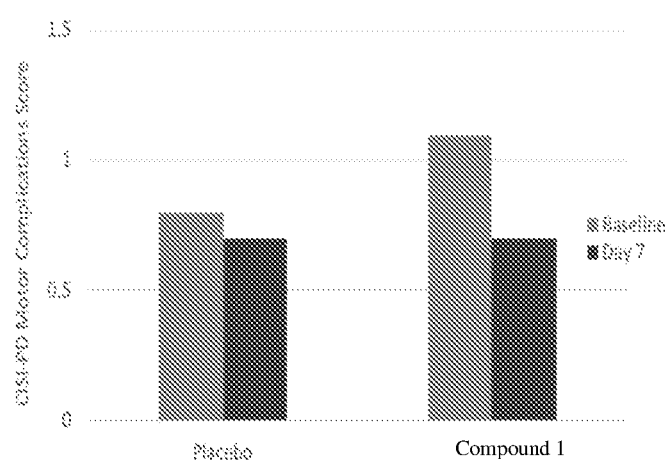
FIG. 4 shows that Compound 1 decreased CISI-PD (Clinical Impression of Severity Index for PD) Motor Complications Score versus placebo.

The efficacy of Compound 1 in improving motor and non-motor symptoms of PD is measured using multiple scales, providing input from both subjects and site raters. Motor performance was improved and motor complications were reduced in the "On" state by Compound 1 relative to placebo treatment as assessed by the Movement Disorder Society Unified Parkinson's Disease Rating Scale (MDS-UPDRS) (FIG. 1). Compound 1 reduces scores on the MDS-UPDRS total scale and 2 subscales: clinician ratings of the motor manifestations of PD, and motor complications including dyskinesias. In addition, Compound 1 reduces dyskinesia symptoms as measured by the Unified Dyskinesia Rating Score (UDysRS) (FIG. 2) and increased total On time and On time without dyskinsias as rated by subjects using the Hauser Patient Motor Diary. (FIGS. 3-4).

These results confirm that inhibitors of PDE1 enhance intracellular signaling by preventing breakdown of cyclic nucleotides (i.e., cAMP, cGMP). Previous studies have shown PDE1 inhibitors potentiate the positive effects of L-DOPA on motor performance. In this trial, Compound 1 is administered once daily for 7 days with no titration and was shown to have a favorable safety profile. The compound is generally well tolerated across a broad range of doses from 1 mg to 90 mg. PDE1 administration is shown to result in reductions in motor symptoms and motor complications on several rater-based and subject-based scales. Significantly, these results suggest that administration of a PDE1 inhibitor, particularly Compound 1, could enhance the effect of dopamine replacement therapy in PD patients, while simultaneously mitigating the known side effects of such treatments.

What is claimed is:

1. A method of mitigating a side effect of a dopamine replacement therapy, the method comprising administering a pharmaceutically effective amount of a PDE1 inhibitor to a subject in need thereof, wherein the dopamine replacement therapy is administered to treat Parkinson's disease, wherein the side effect of the dopamine replacement therapy comprises motor fluctuation and dyskinesia, and wherein the PDE1 inhibitor is a compound according to:
A) Formula I:

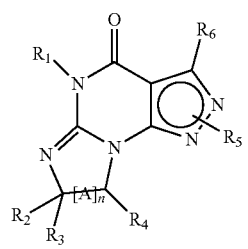

Formula I wherein
(i) R₁ is H or C₁₋₄ alkyl;
(ii) R₄ is H or C₁₋₄ alkyl and R₂ and R₃ are, independently, H or C₁₋₄ alkyl aryl, heteroaryl, (optionally hetero) arylalkoxy, or (optionally hetero) arylalkyl; or
R₂ is H and R₃ and R₄ together form a di-, tri- or tetramethylene bridge;
(iii) R₅ is a substituted heteroarylalkyl;
or R₅ is attached to one of the nitrogens on the pyrazolo portion of Formula I and is a moiety of Formula A Formula A wherein X, Y and Z are, independently, N or C, and R₈, R₉, R₁₁ and R₁₂ are independently H or halogen, and R₁₀ is halogen, alkyl, cycloalkyl, haloalkyl, aryl, heteroaryl optionally substituted with halogen, diazolyl, triazolyl, tetrazolyl, arylcarbonyl (e.g., benzoyl), alkylsulfonyl, heteroarylcarbonyl, or alkoxycarbonyl; provided that when X, Y, or Z is nitrogen, R₈, R₉, or R₁₀, respectively, is not present; and
(iv) R₆ is H, alkyl, aryl, heteroaryl, arylalkyl, arylamino, heterarylamino, N,N-dialkylamino, N,N-diarylamino, or N-aryl-N-(arylakyl) amino; and
(v) n=0 or 1;
(vi) when n=1, A is —C(R₁₃R₁₄)—
wherein R₁₃ and R₁₄, are, independently, H or C₁₋₄ alkyl, aryl, heteroaryl, (optionally hetero) arylalkoxy or (optionally hetero) arylalkyl;

B) Formula II:

Formula II (i) X is C₁₋₆alkylene;
(ii) Y is a single bond, alkynylene, arylene or heteroarylene;
(iii) Z is H, aryl, heteroaryl, halo, haloC₁₋₆alkyl, —C(O)—R¹, —N(R²)(R³), or C₃₋₇cycloalkyl optionally containing at least one atom selected from a group consisting of N or O;
(iv) R¹ is C₁₋₆alkyl, haloC₁₋₆alkyl, —OH or —OC₁₋₆alkyl;
(v) R² and R³ are independently H or C₁₋₆alkyl;
(vi) R⁴ and R⁵ are independently H, C₁₋₆alky or aryl optionally substituted with one or more halo, hydroxy, or C₁₋₆alkoxy;

(vii) wherein X, Y and Z are independently and optionally substituted with one or more halo, C₁₋₆alkyl, haloC₁₋₆alkyl;

C) Formula III:

Formula III wherein
(i) R1 is H or C₁₋₄ alkyl;
(ii) R₂ and R₃ are independently H or C₁₋₆ alkyl;
(iii) R₄ is H or C₁₋₄ alkyl;
(iv) R₅ is aryl optionally substituted with one or more groups independently selected from —C(=O)—C₁₋₆ alkyl and C₁₋₆-hydroxyalkyl;
(v) R₆ and R₇ are independently H or aryl optionally substituted with one or more groups independently selected from C₁₋₆ alkyl and halogen, for example unsubstituted phenyl or phenyl substituted with one or more halogen or phenyl substituted with one or more C₁₋₆ alkyl and one or more halogen or phenyl substituted with one C₁₋₆ alkyl and one halogen; and
(vi) n is 1, 2, 3, or 4;

D) Formula IV:

Formula IV in free or salt form, wherein
(vi) R₁ is C₁₋₄alkyl, or —NH(R₂), wherein R₂ is phenyl optionally substituted with halo;
(vii) X, Y and Z are, independently, N or C;
(viii) R₃, R₄ and R₅ are independently H or C₁₋₄alkyl; or R₃ is H and R₄ and R₅ together form a tri-methylene bridge,
(ix) R₆, R₇ and R₈ are independently:
H,
C₁₋₄alkyl,
pyrid-2-yl substituted with hydroxy, or
—S(O)₂—NH₂;
Provided that when X, Y and/or Z are N, then R₆, R₇ and/or R₈, respectively, are not present; and when X, Y and Z are all C, then at least one of R₆, R₇ or R₈ is —S(O)₂—NH₂ or pyrid-2-yl substituted with hydroxy,
in free, salt or prodrug form, including its enantiomers, diastereoisomers and racemates.

2. The method according to claim 1, wherein the PDE1 inhibitor is:

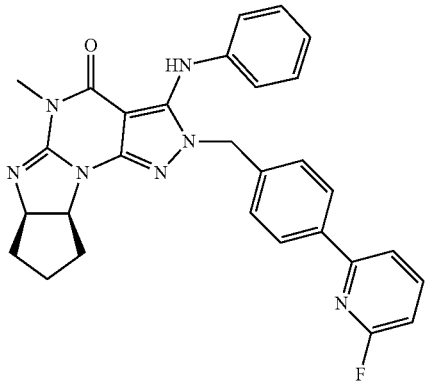 [SMILES: CN1C(=O)c2c(nn(Cc3ccc(-c4cccc(F)n4)cc3)c2Nc2ccccc2)N2C1=N[C@@H]1CCC[C@@H]12]

in free or pharmaceutically acceptable salt form.

3. The method according to claim 1, wherein the PDE1 inhibitor is:

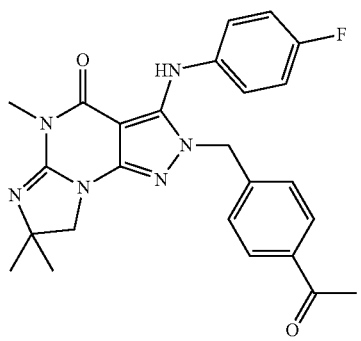 [SMILES: CC(=O)c1ccc(Cn2nc3c(c2Nc2ccc(F)cc2)C(=O)N(C)C2=NC(C)(C)CN23)cc1]

in free or pharmaceutically acceptable salt form.

4. The method according to claim 1, wherein the PDE1 inhibitor is:

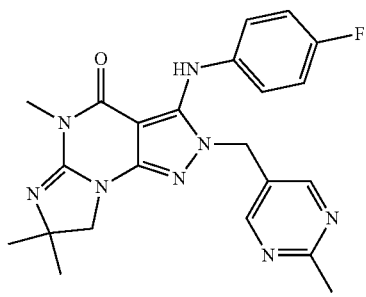 [SMILES: Cc1ncc(Cn2nc3c(c2Nc2ccc(F)cc2)C(=O)N(C)C2=NC(C)(C)CN23)cn1]

in free or pharmaceutically acceptable salt form.

5. The method according to claim 1, wherein the PDE1 inhibitor is:

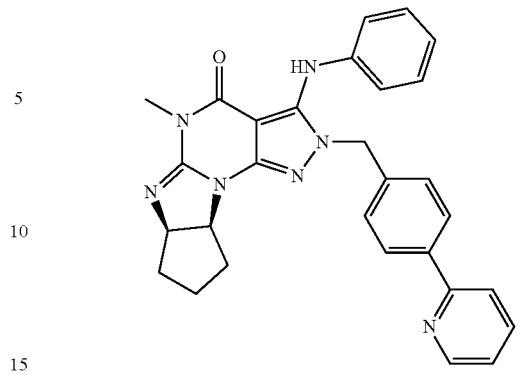

in free or pharmaceutically acceptable salt form.

6. The method according to claim 1, wherein the dopamine replacement therapy comprises administration of a dopaminergic agonist, anticholinergic agents, monoamine oxidase (MAO)-B inhibitors, catechol-O-methyl transferase (COMT) inhibitors, antiparkinson agents, and combinations thereof.

7. The method according to claim 1, wherein administering the PDE1 inhibitor reduces or eliminates the occurrence of the side effects.

8. The method according to claim 1, wherein administration of the PDE1 inhibitor improves motor performance and reduces motor complications in the "On" state relative to placebo treatment as assessed by the Movement Disorder Society Unified Parkinson's Disease Rating Scale (MDS-UPDRS).

9. The method according to claim 1, wherein administration of the PDE1 inhibitor reduces dyskinesia symptoms as measured by the Unified Dyskinesia Rating Score (UDysRS) and increases total "On" time and "On" time without dyskinsias as rated by subjects using the Hauser Patient Motor Diary.

10. The method according to claim 1, wherein the subject is suffering from mild to moderate Parkinson's Disease.

11. The method according to claim 1, wherein the PDE1 inhibitor is administered once daily at a dosage of 1 mg, 3, mg, 10 mg, 30 mg, or 90 mg.

12. The method according to claim 6, wherein the dopaminergic agonist is selected from the group consisting of levodopa (L-dopa), carbidopa, apomorphine, pramipexole, ropinirole, amantadine, rotigotine).

13. The method according to claim 6, wherein the anticholinergic agents are selected from the group consisting of antipsychotics, atropine, benztropine, benzotropine mesylate, biperiden, chlorpeniramine, citalopram, sertraline, dicyclomine, dimenhydrinate, diphenhydramine, doxepin, doxylamine, glycopyrrolate, glycopyrrolium, ipratropium, orphenadrine, oxitropium, oxybutynin, promethazine, propantheline bromide, tolterodine, tiotropium, tricyclic antidepressants, trihexyphenidyl, scopolamine, solifenacin, tropicamide.

14. The method according to claim 13, wherein the antipsychotics are selected from the group consisting of clozapine and quetiapine.

15. The method according to claim 6, wherein the monoamine oxidase (MAO)-B inhibitors are selected from the group consisting of isocarboxazid, nialamide, phenelzine, hydracarbazine, tranylcypromine, rasagiline, selegiline, and safinamide.

16. The method according to claim 6, wherein the catechol-O-methyl transferase (COMT) inhibitors are selected from the group consisting of entacapone, tolcapone, opicapone, nitecapone.

17. The method according to claim 6, wherein the antiparkinson agents are selected from SSIAs.

18. The method according to claim 17, wherein the SSIA is pimavanserin.

* * * * *

UNITED STATES PATENT AND TRADEMARK OFFICE
CERTIFICATE OF CORRECTION

PATENT NO. : 12,194,042 B2
APPLICATION NO. : 17/287478
DATED : January 14, 2025
INVENTOR(S) : Robert E. Davis et al.

Page 1 of 1

It is certified that error appears in the above-identified patent and that said Letters Patent is hereby corrected as shown below:

In the Claims

In Column 35, Lines 27-28, in Claim 1:
"arylcarbonyl (e.g., benzoyl)" should be corrected to "arylcarbonyl".

In Column 38, Line 38, in Claim 9:
"without dyskinsias" should be corrected to "without dyskinesia".

In Column 38, Line 49, in Claim 12:
"rotigotine)" should be corrected to "rotigotine".

Signed and Sealed this
Twenty-second Day of April, 2025

Coke Morgan Stewart
*Acting Director of the United States Patent and Trademark Office*